United States Patent
Chu et al.

(10) Patent No.: US 9,803,179 B2
(45) Date of Patent: Oct. 31, 2017

(54) MUTANT CYANOBACTERIA AND METHOD TO ENHANCE PHOTOSYNTHETIC GROWTH AND BIOMASS PRODUCTION OF CYANOBACTERIA

(71) Applicant: Academia Sinica, Taipei (TW)

(72) Inventors: Hsiu-An Chu, Taipei (TW); Jine-Yung Huang, New Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/820,866

(22) Filed: Aug. 7, 2015

(65) Prior Publication Data

US 2016/0060604 A1    Mar. 3, 2016

Related U.S. Application Data

(60) Provisional application No. 62/034,337, filed on Aug. 7, 2014.

(51) Int. Cl.
*C07K 14/195* (2006.01)
*C12N 9/02* (2006.01)

(52) U.S. Cl.
CPC .......... *C12N 9/0008* (2013.01); *C07K 14/195* (2013.01)

(58) Field of Classification Search
None
See application file for complete search history.

(56) References Cited

PUBLICATIONS

Hung et al., J. Biol. Chem., 285 (8); 5653-5663, 2010.*
Guerrero et al., Biochim. Biophys. Acta, 1837:908-919, 2014.*
Hung et al., Biochim. Biophys. Acta, 1767:686-693, 2007.*

* cited by examiner

*Primary Examiner* — Nancy Treptow
(74) *Attorney, Agent, or Firm* — Wolf, Greenfield & Sacks, P.C.

(57) ABSTRACT

The present invention relates to a mutant cyanobacterium and a method to increase photosynthetic growth and/or biomass production of cyanobacteria by using the same.

15 Claims, 14 Drawing Sheets

| Strains | % of Density of Bands |
|---|---:|
| WT-M | 100 |
| A16FJ-M | 114±20 |
| S28Vβ-M | 105±12 |
| V32Fβ-M | 147±11 |
| WT-MP | 100 |
| A16FJ-MP | 110±1 |
| S28Vβ-MP | 101±11 |
| V32Fβ-MP | 91±13 | psbE

| | |
|---|---|
| Synechocystis PCC6803 | : --SGTTGERPFSDIVTSIRYWVIHSITIPMLFIAGWLFVSTGLAYDAFGTPRPDEYFTQTRQELPILQERYDINGEIQEFNQ- (SEQ ID NO: 1) |
| Cyanothece PCC7822 | : -MSGTTGERPFSDIVTSIRYWVIHSITIPMLFIAGWLFVSTGLAYDVFGTPRPDQYFTQDRLELPILKERYNTDQQIKEFNK- (SEQ ID NO: 11) |
| Anabaena ATCC29413 | : -MSGTTGERPFSDIVTSIRYWVIHSITIPALFIAGWLFVSTGLAYDVFGTPRPDEYYTQARQELPIVNNRFEAKKQVEQLIQK (SEQ ID NO: 12) |
| Arthrospira platensis | : -MAGTTGERPFGDIITSVRYWVIHSLTIPALFIAGWLFVSTGLAYDAFGTPRPNEYFTQERQELPIITERQDSKTQIQQFIAK (SEQ ID NO: 13) | psbF

| | |
|---|---|
| Synechocystis PCC6803 | : -AT-GNPNQPVTYPIFTVRWLAVHTLAVPSVFFVGAIAAMQFIQR (SEQ ID NO: 2) |
| Cyanothece PCC7822 | : MAN-TTGNQPVSYPIFTVRWLAVHTLAVPTVFFIGAIAAMQFIQR (SEQ ID NO: 14) |
| Anabaena ATCC29413 | : MTSGNNINQPVTYPIFTVRWLAVHTLAVPTVFFLGAIASMQFIQR (SEQ ID NO: 15) |
| Arthrospira platensis | : MTN-ANQNQPITYPIFTVRWLAVHTLAVPTVFFLGAIAAMQFIQR (SEQ ID NO: 16) | psbJ

| | |
|---|---|
| Synechocystis PCC6803 | : -MFAE----------------GRIPLWVGVVAGIGAIGVLGLFFYGAYAGLGSSM (SEQ ID NO: 3) |
| Cyanothece PCC7822 | : -MFAE----------------GRIPLWVAVVAGLGVIAVVGLFFYGAYAGLGSSL (SEQ ID NO: 17) |
| Anabaena ATCC29413 | : MLLREEKAVSAGS--------GRIPLWVVATIAGLGVITVVGIFFYGAYAGLGSSI (SEQ ID NO: 18) |
| Arthrospira platensis | : -MSG-------DAK-------LPLWLIATVAGTGVLVVVGLFFYGAYVGVGSAL (SEQ ID NO: 19) |

Fig. 7

MUTANT CYANOBACTERIA AND METHOD TO ENHANCE PHOTOSYNTHETIC GROWTH AND BIOMASS PRODUCTION OF CYANOBACTERIA

RELATED APPLICATION

The present application claims priority under 35 U.S.C. §119(e) to U.S. Provisional Patent Application No. 62/034,337, filed Aug. 7, 2014, the content of which is herein incorporated by reference in its entirety.

TECHNOLOGY FIELD

The present invention relates to a mutant cyanobacterium and a method to increase photosynthetic growth and/or biomass production of cyanobacteria by using the same.

BACKGROUND OF THE INVENTION

Photosystem II (PSII) is a large membrane protein complex in the thylakoid membrane of plants and cyanobacteria [1-4]. It utilizes light energy to oxidize water on the lumen side and to reduce plastoquinone (PQ) on the stromal side of the thylakoid membrane [1-4]. However, photosystem II (PSII) is the major target for the light-induced damage of the photosynthetic apparatus under excess light conditions [5,6]. To avoid this problem, photosynthetic organisms have developed several distinct and sophisticated photo-protective mechanisms to ensure their survival under excess light conditions [5,6]. In higher plants, excess light energy is dissipated in PSII light-harvesting antenna (LHCII) as heat that reduces the amount of excitation energy reaching the reaction center and protects PSII from photo-damage. This process (also called nonphotochemical fluorescence quenching; NPQ) involves the activation of the xanthophyll cycle and the conformational change of LHCII which are controlled by the formation of $\Delta pH$ in the lumen of PSII [5,6]. In contrast, cyanobacteria use phycobilisomes as antenna to capture sunlight. A great number of cyanobacteria develop a distinct blue-green-light-induced NPQ mechanism to cope with high-light stress [8-10]. When exposed to high intensity of white light or blue light, a soluble orange carotenoid protein (OCP) will undergo photo-conversion into the active red form. The red form of OCP is able to interact with the allophycocyanin (APC) core of the phycobilisome and induce the NPQ effect which dissipates excess excitation energy on the phycobilisome as heat, thereby protecting PSII reaction centers against photodamage (7-17). During this process, the OCP acts as the light sensor, the signal propagator and the energy quencher. When the intensity of the blue light or white light is decreased, the binding between the red form of OCP and APC core of the phycobilisome is released with the help of fluorescence recovery protein (FRP). The FRP interacts with the C-terminal domain of the red form of OCP and accelerates its conversion to orange form and detach from the phycobilisome to stop the NPQ process (14). In contrast to the photoprotective mechanisms in higher plants and algae, up to now there is no evidence for the feed-back regulation of PSII in the OCP-mediated photoprotective mechanism in cyanobacteria.

The 2.9 Å resolution x-ray crystallographic structural models of PSII from the cyanobacteria Thermosynechococcus elongatus revealed a newly discovered PQ molecule ($Q_C$) and its diffusion channel [3, 18]. The head-group $Q_C$ molecule locates in a very hydrophobic cavity surrounded by the tails of lipids, $Q_B$ and a Car molecule; the tail of $Q_C$ molecule situates in a hydrophobic channel, surrounded by the trans-membrane helixs of cytochrome (Cyt) $b_{559}$ α and β subunits (encoded by psbE and psbF genes, respectively) and PsbJ, which is open toward the internal space of thylakoid membranes [3, 18]. The occupancy of this $Q_C$ site by PQ (or PQH$_2$) was proposed to be involved in exchange of PQ/PQH$_2$ on the $Q_B$ site from the pool [3, 18] or to modulate the redox potential and the reactivity of Cyt $b_{559}$ [3, 18-20, also see ref 21 for a different view]. In addition, the $Q_C$ site was also proposed as the catalytic site for PQH$_2$ oxidase activity of Cyt $b_{559}$ [22-29]. However, occupancy of the $Q_C$ site was not observed in the recent 1.9 Å resolution crystal structural models of PSII from T. vulcanus [2]. The function of $Q_C$ remains elusive.

WO 2012/092033 describes enhancement of biomass production in a photosynthetic microorganism by disruption of NPQ process via disrupting the production of at least one carotenoid and/or reducing the expression of at least one carotenoid binding protein, and suggests that reduction of NPQ allows a higher proportion of photons to provide energy for photochemistry and biochemical pathways that generate biomass. However, it has been reported that cyanobacterial photoactive orange carotenoid protein has new function in singlet oxygen quencher in thylakoid membrane in addition to energy quencher function (Sedoud et al, plant cell (2014) 26, 1781-1791). Therefore, disruption of NPQ process via disrupting the production of at least one carotenoid and/or reducing the expression of at least one carotenoid binding protein in cyanobacteria may lead to susceptible photoinhibition, which is light-induced reduction in the photosynthetic capacity, due to the disruption of the dual-photoprotective functions of orange carotenoid protein (plant cell (2006)).

SUMMARY OF THE INVENTION

In this invention, it is unexpectedly found that some newly constructed mutant cyanobacterial cells with a point mutation on cytochrome b559 α or β subunit or PsbJ show enhanced effects of state transitions under medium blue-light conditions and weakened effects of nonphotochemical fluorescence quenching (NPQ) under strong blue-light conditions, without affecting the expression of an OCP. It is further demonstrated that some of the mutant cyanobacteria exhibit increased photosynthetic growth and biomass productions as compared to wild-type cells under normal growth conditions, which may thus be valuable in biomass production for use in a variety of applications such as bioenergy applications and commercial productions for biofuel, food, feed and other valuable commercial products.

In general, the present invention provides mutant cyanobacterial cells with a mutation on cytochrome b559 α or β subunits or PsbJ, especially near the opening of the proposed Qc transfer channel in PSII, which exhibit increased photosynthetic growth and biomass productions as compared to wild-type cells.

Particularly, in one aspect, the present invention provides a mutant cyanobacterium expressing a mutant cytochrome polypeptide selected from the group consisting of:

(a) a mutant cytochrome b559 α polypeptide having an amino acid substitution with alanine (A) at a position corresponding to position 23 in a cytochrome b559 α polypeptide having SEQ ID NO: 1;

(b) a mutant cytochrome b559 β polypeptide having an amino acid substitution with alanine (A) or valine (V) at a position corresponding to position 28 in a cytochrome b559 β polypeptide having SEQ ID NO: 2, or an amino acid substitution with phenylalanine (F) at a position corresponding to position 32 in a cytochrome b559 β polypeptide having SEQ ID NO: 2; and (c) a mutant cytochrome PsbJ polypeptide having an amino acid substitution with phenylalanine (F) or arginine (R) at a position corresponding to position 16 in a cytochrome PsbJ polypeptide having SEQ ID NO: 3, or an amino acid substitution with phenylalanine (F) at a position corresponding to position 20 in a cytochrome PsbJ polypeptide having SEQ ID NO: 3.

Specifically, the mutant cyanobacterium of the invention exhibits one or more beneficial characteristics including (1) inhibited nonphotochemical fluorescence quenching (NPQ), (2) accelerated dark recovery of NPQ, (3) a normal amount of OCP, and/or (4) increased photosynthetic growth rate and/or biomass production, when compared with a wild type cyanobacteria without any of the mutations under the same conditions.

In some embodiments, the mutant cytochrome polypeptide as described herein comprise a mutation selected from the group consisting of S23Aα, S28Aβ, S28Vβ, V32Fβ, A16FJ, A16RJ and A20FJ.

In some embodiments, the mutant cyanobacterium comprises a cytochrome b559 α gene (psbE) encoding SEQ ID NO: 4.

In some embodiments, the mutant cyanobacterium comprises a cytochrome b559 β gene (psbF) encoding SEQ ID NO: 5, 6 or 7.

In some embodiments, the mutant cyanobacterium comprises a cytochrome PsbJ gene (psbJ) encoding SEQ ID NO: 8, 9 or 10.

In some embodiments, the mutant cyanobacterium can be made from a species of the genera, which include but are not limited to *Agmenellum, Anabaenopsis, Anabaena, Anacystis, Arthrospira, Aphanizomenon, Asterocapsa, Borzia, Calothrix, Chamaesiphon, Chlorogloeopsis, Chroococcus, Chroococcidiopsis, Crinalium, Cyanobacterium, Crocosphaera, Cyanobium, Cyanocystis, Cyanospira, Cyanothece, Cylindrospermopsis, Cylindrospermum, Dactylococcopsis, Dermocarpella, Fischerella, Fremyella, Geitleria, Gloeobacter, Geitlerinema, Gloeocapsa, Gloeothece, Halospirulina, Iyengariella, Leptolyngbya, Lyngbya, Limnothrix, Microcoleus, Myxosarcina, Microcystis, Nodularia, Nostoc, Nostochopsis, Oscillatoria, Phormidium, Pleurocapsa, Planktothrix, Prochlorococcus, Prochloron, Prochlorothrix, Pseudanabaena, Rivularia, Schizothrix, Spirulina, Scytonema, Stanieria, Starria, Symploca, Stigonema, Synechococcus, Synechocystis, Thermosynechococcus, Trichodesmium, Tolypothrix, Tychonema,* and *Xenococcus* genus.

In some certain embodiments, the mutant cyanobacterium is a species of the genera selected from the group consisting of *Synechocystis, Synechococcus, Arthrospira, Nostoc, Anabaena, Thermosynechococcus,* and *Cyanothece.*

In another aspect, the present invention provides a method for producing biomass or a biomolecule comprising culturing a mutant cyanobacterium as described herein under light conditions in a suitable medium and harvesting biomass or a biomolecule from the culture.

In some embodiments, the biomolecule is selected from the group consisting of carbohydrates, fatty acids, proteins, amino acids, peptide, pigments, terpenoid, carotenoid, vitamin, or other high-value biomolecule.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

(FIG. 1B) wild-type (black trace), S23Aα (blue trace), and S28Aβ Cyt $b_{559}$ mutant cells (red trace) by chlorophyll a fluorescence measurement. Conditions: 20 μg of chlorophyll in 2 mL of BG-11 medium. Samples were incubated in darkness for 1 min. The levels of Fo and Fm was normalized.

(FIG. 5A) with 10 mM DCMU, (FIG. 5B) with 10 mM DBMIB, (FIG. 5C) no addition, (FIG. 5D) plus red actinic light. The intensity of the blue actinic light was ~250 μE $m^{-2}$ $s^{-1}$. The intensity of red actinic light in (FIG. 5D) was ~50-60 μE $m^{-2}$ $s^{-1}$. The other conditions were the same as in FIGS. 2A-2E.

FIG. 7 shows the alignment of the amino acid sequences of (a) a cytochrome b559 α polypeptide (b) a cytochrome b559 β polypeptide and (c) a cytochrome PsbJ polypeptide, of *Synechocystis* PCC6803, *Cyanothece* PCC7822, *Anabaena* ATCC29413, and *Arthropira platensis.*

DETAILED DESCRIPTION OF THE INVENTION

Figure 1A:
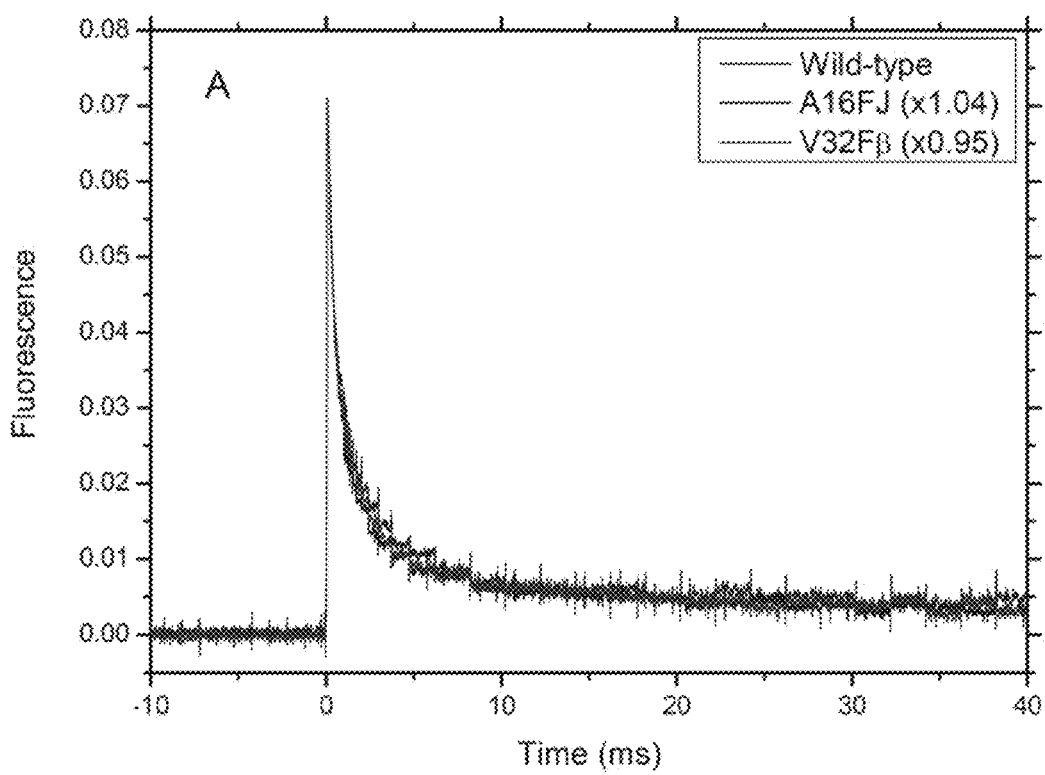
FIGS. 1A-1B show the kinetics of electron transfer from $Q_A^-$ to $Q_B$ and $Q_B^-$ in response to a saturating flash given to (FIG. 1A) wild-type (black trace), A16FJ (blue trace), and V32Fβ mutant cells (green trace)

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a component" includes a plurality of such components and equivalents thereof known to those skilled in the art.

The term "polynucleotide" or "nucleic acid" refers to a polymer composed of nucleotide units. Polynucleotides include naturally occurring nucleic acids, such as deoxyribonucleic acid ("DNA") and ribonucleic acid ("RNA") as well as nucleic acid analogs including those which have non-naturally occurring nucleotides. Polynucleotides can be synthesized, for example, using an automated DNA synthesizer. The term "nucleic acid" typically refers to large polynucleotides. It will be understood that when a nucleotide sequence is represented by a DNA sequence (i.e., A, T, G, C), this also includes an RNA sequence (i.e., A, U, G, C) in which "U" replaces "T." The term "cDNA" refers to a DNA that is complementary or identical to an mRNA, in either single stranded or double stranded form.

The term "complementary" refers to the topological compatibility or matching together of interacting surfaces of two polynucleotides. Thus, the two molecules can be described as complementary, and furthermore the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'."

The term "encoding" refers to the inherent property of specific sequences of nucleotides in a polynucleotide (e.g., a gene, a cDNA, or an mRNA) to serve as templates for synthesis of other polymers and macromolecules in biological processes having either a defined sequence of nucleotides (i.e., rRNA, tRNA and mRNA) or a defined sequence of amino acids and the biological properties resulting therefrom. Therefore, a gene encodes a protein if transcription and translation of mRNA produced by that gene produces the protein in a cell or other biological system. It is understood by a skilled person that numerous different polynucleotides and nucleic acids can encode the same polypeptide as a result of the degeneracy of the genetic code. It is also understood that skilled persons may, using routine techniques, make nucleotide substitutions that do not affect the polypeptide sequence encoded by the polynucleotides described there to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "recombinant polynucleotide" refers to a polynucleotide or nucleic acid having sequences that are not naturally joined together. A recombinant nucleic acid may be present in the form of a vector. "Vectors" may contain a given nucleotide sequence of interest and a regulatory sequence. Vectors may be used for expressing the given nucleotide sequence or maintaining the given nucleotide sequence for replicating it, manipulating it or transferring it between different locations (e.g., between different organisms). Vectors can be introduced into a suitable host cell for the above mentioned purposes.

As used herein, the term "operably linked" may mean that a polynucleotide is linked to an expression control sequence in such a manner to enable expression of the polynucleotide when a proper molecule (such as a transcriptional factor) is bound to the expression control sequence.

As used herein, the term "expression control sequence" or "regulatory sequence" means a DNA sequence that regulates the expression of the operably linked nucleic acid sequence in a certain host cell.

Examples of vectors include, but are not limited to, plasmids, cosmids, phages, YACs or PACs. Typically, in vectors, the given nucleotide sequence is operatively linked to the regulatory sequence such that when the vectors are introduced into a host cell, the given nucleotide sequence can be expressed in the host cell under the control of the regulatory sequence. The regulatory sequence may comprises, for example and without limitation, a promoter sequence (e.g., the cytomegalovirus (CMV) promoter, simian virus 40 (SV40) early promoter, T7 promoter, and alcohol oxidase gene (AOX1) promoter), a start codon, a replication origin, enhancers, an operator sequence, a secretion signal sequence (e.g., α-mating factor signal) and other control sequence (e.g., Shine-Dalgano sequences and termination sequences). Preferably, vectors may further contain a marker sequence (e.g., an antibiotic resistant marker sequence) for the subsequent screening procedure. For purpose of protein production, in vectors, the given nucleotide sequence of interest may be connected to another nucleotide sequence other than the above-mentioned regulatory sequence such that a fused polypeptide is produced and beneficial to the subsequent purification procedure. Said fused polypeptide includes, but is not limited to, a His-tag fused polypeptide and a GST fused polypeptide.

As used herein, the term "polypeptide" refers to a polymer composed of amino acid residues linked via peptide bonds, for example, containing about 300 or less, 250 or less, 200 or less, 150 or less, 100 or less, 80 or less amino acid residues. Amino acids can be expressed by three letters or one letter as known in the art.

To determine the percent identity of two amino acid sequences, the sequences are aligned for optimal comparison purposes (e.g., gaps can be introduced in the sequence of a first amino acid sequence for optimal alignment with a second amino acid sequence). In calculating percent identity, typically exact matches are counted. The determination of percent homology or identity between two sequences can be accomplished using a mathematical algorithm known in the art, such as BLAST and Gapped BLAST programs, the NBLAST and XBLAST programs, or the ALIGN program.

A "mutant" cell as used herein can mean a cell expressing a modified (i.e. mutant) protein/polypeptide or having a gene which differs from the wild-type protein/polypeptide or gene. A mutant protein or polypeptide refer to a protein or a polypeptide whose amino acid sequence is altered by substitution, deletion or addition of one or more amino acid residues compared to the amino acid sequence of a native or wild-type protein. Specifically, a point substitution can be that a single amino acid at a position has been changed to another amino acid, in the sequence of the naturally-occurring protein.

A cytochrome b559 α polypeptide as used herein refers to a component of the PSII complex which is encoded by a cytochrome PsbE gene. In one embodiment, a cytochrome b559 α polypeptide in wild-type cyanobacteria, Synechocystis sp. has the amino acid sequence of SEQ ID NO: 1; the amino acid residue at position 23 is serine (S). In other embodiments, a cytochrome b559 α polypeptide in other wild-type cyanobacteria species has the amino acid sequence as shown in SEQ ID NO: 11, 12 or 13 (see FIG. 7).

A cytochrome b559 β polypeptide as used herein means a component of the PSII complex which is encoded by a cytochrome PsbF gene. In one embodiment, a cytochrome b559 β polypeptide in wild-type cyanobacteria, *Synechocystis* sp. has the amino acid sequence of SEQ ID NO: 2; the amino acid residue at position 28 is serine (S) and the amino acid residue at position 32 is valine (V). In other embodiments, a cytochrome b559 β polypeptide in other wild-type cyanobacteria species has the amino acid sequence as shown in SEQ ID NO: 14, 15 or 16 (see FIG. 7).

A cytochrome PsbJ polypeptide as used herein means a component of the PSII complex which is encoded by a cytochrome PsbJ gene. In one embodiment, a cytochrome PsbJ polypeptide in wild-type cyanobacteria, *Synechocystis* sp. has the amino acid sequence of SEQ ID NO: 3; the amino acid residue at positions 16 and 20 is alanine (A). In other embodiments, a cytochrome PsbJ polypeptide in other wild-type cyanobacteria species has the amino acid sequence as shown in SEQ ID NO: 17, 18 or 19 (see FIG. 7).

According to the present invention, mutant cyanobacterial cells with a mutation on cytochrome b559 α or β subunits or PsbJ, especially near the opening of the proposed Qc transfer channel in PSII, are provided, which exhibit increased photosynthetic growth and biomass productions as compared to wild-type cells.

Particularly, the mutant cyanobacterial cells of the invention expressing a mutant cytochrome polypeptide selected from the group consisting of:

(a) a mutant cytochrome b559 α polypeptide having an amino acid substitution with alanine (A) at a position corresponding to position 23 in a cytochrome b559 α polypeptide having SEQ ID NO: 1;

(b) a mutant cytochrome b559 β polypeptide having an amino acid substitution with alanine (A) or valine (V) at a position corresponding to position 28 in a cytochrome b559 β polypeptide having SEQ ID NO: 2, or an amino acid substitution with phenylalanine (F) at a position corresponding to position 32 in a cytochrome b559 β polypeptide having SEQ ID NO: 2; and (c) a mutant cytochrome PsbJ polypeptide having an amino acid substitution with phenylalanine (F) or arginine (R) at a position corresponding to position 16 in a cytochrome PsbJ polypeptide having SEQ ID NO: 3, or an amino acid substitution with phenylalanine (F) at a position corresponding to position 20 in a cytochrome PsbJ polypeptide having SEQ ID NO: 3.

Specifically, the mutant cytochrome polypeptide as described herein comprising a mutant is selected from the group consisting of S23Aα, S28Aβ, S28Vβ, V32Fβ, A16FJ, A16RJ and A20FJ.

In some embodiments, the mutant cyanobacterial cells of the invention comprises a gene (psbE) encoding a mutant cytochrome b559 α polypeptide of SEQ ID NO: 4 wherein the amino acid residue at position 23 is changed to alanine (A), as compared to the wild type sequence (SEQ ID NO: 1) wherein the amino acid residue at position 23 is serine (S).

In some embodiments, the mutant cyanobacterial cells of the invention comprises a gene (psbF) encoding a mutant cytochrome b559 β polypeptide of SEQ ID NO: 5 or 6 wherein the amino acid residue at position 28 is changed to alanine (A) or valine (V), as compared to the wild type sequence (SEQ ID NO: 2).

In some embodiments, the mutant cyanobacterial cells of the invention comprises a gene (psbF) encoding a mutant cytochrome b559 β polypeptide of SEQ ID NO: 7 wherein the amino acid residue at position 32 is changed to phenylalanine (F), as compared to the wild type sequence (SEQ ID NO: 2).

In some embodiments, the mutant cyanobacterial cells of the invention comprises a gene (psbJ) encoding a mutant cytochrome PsbJ polypeptide of SEQ ID NO: 8 or 9 wherein the amino acid residue at position 16 is changed to phenylalanine (F) or arginine (R) as compared to the wild type sequence (SEQ ID NO: 3).

In some embodiments, the mutant cyanobacterial cells of the invention comprises a gene (psbJ) encoding a mutant cytochrome PsbJ polypeptide of SEQ ID NO: 10 wherein the amino acid residue at position 20 is changed to phenylalanine (F) as compared to the wild type sequence (SEQ ID NO: 3).

The mutant cyanobacterial cells of the invention can be prepared by a routine mutagenesis method as known in the art [30, 31]. Specifically, mutation on a specific amino acid residue is introduced into a proper plasmid by oligonucleotide-derived mutagenesis, the resultant mutant plasmid is then introduced into host cells by transformation, and mutant cells are selected on solid media with antibiotics until their mutated gene is completely segregated, which can be confirmed by PCR.

Examples of the mutant cyanobacterium of the invention can be a species of the genera, including but not limited to, *Agmenellum, Anabaenopsis, Anabaena, Anacystis, Arthrospira, Aphanizomenon, Asterocapsa, Borzia, Calothrix, Chamaesiphon, Chlorogloeopsis, Chroococcus, Chroococcidiopsis, Crinalium, Cyanobacterium, Crocosphaera, Cyanobium, Cyanocystis, Cyanospira, Cyanothece, Cylindrospermopsis, Cylindrospermum, Dactylococcopsis, Dermocarpella, Fischerella, Fremyella, Geitleria, Gloeobacter, Geitlerinema, Gloeocapsa, Gloeothece, Halospirulina, Iyengariella, Leptolyngbya, Lyngbya, Limnothrix, Microcoleus, Myxosarcina, Microcystis, Nodularia, Nostoc, Nostochopsis, Oscillatoria, Phormidium, Pleurocapsa, Planktothrix, Prochlorococcus, Prochloron, Prochlorothrix, Pseudanabaena, Rivularia, Schizothrix, Spirulina, Scytonema, Stanieria, Starria, Symploca, Stigonema, Synechococcus, Synechocystis, Thermosynechococcus, Trichodesmium, Tolypothrix, Tychonema,* and *Xenococcus* genus.

In some embodiments, the mutant cyanobacterial cells of the invention can be made from a cyanobacterial species of the genera selected from the group consisting of *Synechocystis, Synechococcus, Arthrospira, Nostoc, Anabaena, Thermosynechococcus,* and *Cyanothece*.

According to the present invention, the mutant cyanobacterium of the invention exhibits one or more beneficial characteristics including (1) inhibited nonphotochemical fluorescence quenching (NPQ), (2) accelerated dark recovery of NPQ, (3) a normal amount of OCP, and/or (4) increased photosynthetic growth rate and/or biomass production, when compared with a wild type cyanobacteria without any of the mutations under the same conditions. The beneficial characteristics as described herein can be measured or determined by routine methods as known in the art.

In certain embodiments, the mutant cyanobacterial cells of the invention (e.g. A16FJ and V32Fβ) exhibits shorten doubling time, i.e. higher photosynthetic growth rates (e.g. about 1.1 folded) and increased biomass accumulation (e.g. about 30-40% higher) than wild-type cells under normal growth conditions.

As another aspect, the present invention also provides a method for producing biomass or a biomolecule comprising culturing a mutant cyanobacterial cells as described herein under light conditions in a suitable medium and harvesting biomass or a biomolecule from the culture.

In some embodiments, the biomolecule is selected from the group consisting of carbohydrates, fatty acids, proteins, amino acids, peptide, pigments, terpenoid, carotenoid, vitamin, or other high-value biomolecules.

In certain embodiments, the mutant cyanobacterial cells are cultured in a normal condition, such as a temperature range from 25 to 45° C. under white light or sunlight, in a photobioreactor or a pond.

The method of the invention is valuable in biomass production for use in a variety of applications such as bioenergy applications and commercial productions for biofuel (e.g. lipid, alcohol or hydrogen), food, feed and other valuable commercial products.

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

EXAMPLES

In our studies, we constructed several cytochrome $b_{559}$ and PsbJ mutant cells of *Synechocystis* PCC 6803 with mutations near the opening of the proposed Qc transfer channel in PSII. Several mutant cells showed severe inhibitory effects on OCP-mediated nonphotochemical fluorescence quenching and significant acceleration on the dark-recovery of fluorescence yield. Our data suggest that mutations on Cyt $b_{559}$ and PsbJ may alter the interaction of the APC core complex with OCP and cause the above effects. In addition, DCMU and DBMIB treatments did not show significant effects on the OCP-mediated photoprotection in wild-type cells. Our results suggested that the OCP-mediated photoprotection was not directly regulated by the redox state of plastoquinone pool. Furthermore, several mutant cells showed increased photosynthetic growth and biomass productions as compared to wild-type cells under normal growth conditions. Our results demonstrate that modulation of OCP-mediated photoprotection in cyanobacteria has the potential to increase biomass production that have the practical applications to enhance the biomass and biofuel production in cyanobacteria.

1. Material and Methods 1.1 Growth and Preparation of *Synechocystis* sp. PCC6803 Cells Wild-type and mutant *Synechocystis* cells were photoautotrophically grown in BG-11 medium. Cultures were propagated at 30 ° C. under growth light conditions with intensity about 30 μmol photons $m^{-2}$ $s^{-1}$. Cultures were continuously bubbled with sterile, humidified air. Liquid cultures in exponential growth ($OD_{730}$ 0.7-1.2) were harvested and used for biochemical and functional analysis.

1.2 Construction of Cyt $b_{559}$ and PsbJ Mutants.

The point mutation on amino acid residues of Cyt $b_{559}$ and PsbJ was introduced into the plasmid PAC559EM® by oligonucleotide-derived mutagenesis according to reference [30, 31]. The mutant was constructed by transformation of the mutant plasmid into the host strain (ΔpsbEFLJ) of *Synechocystis* sp. PCC6803 cells. Mutants were selected on solid media containing the antibiotic Em (0.1 μg/mL) until their mutated gene was completely segregated. Complete segregation of the mutated gene in these mutant cells was verified by PCR.

1.3 Measurement of Photosynthetic Oxygen Evolution.

Steady-state rates of oxygen-evolution were measured with a Clark-type oxygen electrode (YSI model 5331 oxygen probe) fitted with a water-jacketed cell. Concentrated cells were diluted into growth medium held at 25° C. in a stirred, water-jacketed cell. 2 mM potassium ferricyanide and 2 mM 2,6-dichloro-p-benzoquinone (DCBM) were added as artificial electron acceptor to the BG11 medium immediately prior to the addition of the cells. Saturating illumination was provided from both sides of the water-jacketed cell by two fiber-optic illuminators (Dolan-Jenner model MI 150).

1.4 Measurement of Chlorophyll a Fluorescence at 295 K.

Chlorophyll a fluorescence measurements at 295 K were performed with a Dual PAM (pulse-amplitude-modulation) fluorometer (Walz, Germany). The relative PSII content of cells on a chlorophyll basis was estimated from the total yield of variable chlorophyll a fluorescence ($F_{max}$-$F_0$) measured in the presence of DCMU and hydroxylamine, according to the references [31-33]. Experimental conditions for measurements of time-dependent flash-induced transients of PSII fluorescence yield, and the kinetics of electron transfer from $Q_A^-$ to $Q_B$ in response to a saturating flash given to wild-type and mutant cells are described in the FIG. legends.

1.5 MP and M Membrane Preparations

The MP and M thylakoid membranes were isolated according to reference [10].

1.6 Gel Electrophoresis and Western Blots Analysis

MP and M fractions equivalent to 2 μg of chlorophyll were separated by SDS-PAGE on a 12% polyacrylamide/2 M urea gel in a Tris/MES system (Kashino et al., 2001). For the detection of OCP protein, the rabbit antisera specific to OCP were used as the primary antibody (provided by Adjele Wilson) and peroxidase-conjugated goat anti rabbit antibody was used as the secondary antibody (Sigma). Bands were visualized by using Western Lightning Plus-ECL (PerkinElmer).

1.7 Biomass Determination

Cultures were grown photoautotrophically at 30° C. and 30 μmol μE $m^{-2}$ $s^{-1}$ from white fluorescent lights. 100 ml liquid cultures were harvested after 126 hours and concentrated into 5 ml by centrifugation. The 5 ml samples were oven-dried in aluminum dishes for 24 h at 105° C., cooled to room temperature, and the dry weight were measured.

1.8 FT-IR Determination of Biomass Composition in WT and Mutant Cells 30 mL cultures of WT and mutant cells were concentrated and re-suspended to about 50 microliters. Four microliters of the suspension was spread on a silicon ATR sampling plate of ConcentratIR™ Multiple Reflection ATR Accessory (Harrick, USA) and air-dried for 15 min at room temperature. An infrared spectrometer (Bruker Vertex 70, Germany) was used to record the characteristic peak areas of lipid, protein and carbohydrate at 2800-3000 $cm^{-1}$, 1500-1700 $cm^{-1}$ and 1000-1200 $cm^{-1}$, respectively. Biomass composition in WT and mutant cells were analyzed in accordance with the reference cited (Pistorious et al., 2009).

Results 2.1 Growth and Photosynthetic Characteristics of Mutant Cells

Several site-directed mutants of Cyt $b_{559}$ and PsbJ near the opening of the proposed $Q_C$ transfer channel were constructed in the experimental model cyanobacterium *Synechocystis* PCC 6803. The light-saturated oxygen-evolution activity and estimated PSII contents of the mutant strains that are discussed in this study are listed in Table 1. All these mutant cells grew photoautotrophically as wild-type cells. In addition, the maximal oxygen evolution rates and estimated PSII content of these mutant cells were all similar to those of wild-type cells (Table 1).

TABLE 1

General properties of wild-type and mutant cells

| Strain | Photosynthetic Growth | $O_2$ evolution (% of wild-type) | PSII content (% of wild-type) |
|---|---|---|---|
| Wild-type | + | 100% ± 6 | 100% |
| A16FJ | + | 97% ± 5 | 85% ± 8 |
| G19FJ | + | 79% ± 6 | 98% ± 5 |
| A20FJ | + | 93% ± 10 | 103% ± 2 |
| S23Aα | + | 83% ± 1 | 104% ± 2 |
| S23Tα | + | 88% ± 1 | 104% ± 12 |
| S23Vα2 | + | 100% ± 1 | 102% ± 1 |
| S28Aβ | + | 79% ± 5 | 100% ± 0 |
| S28Vβ | + | 86% ± 5 | 87% ± 8 |
| V32Fβ | + | 95% ± 2 | 105% ± 6 |

2.2 Measurement of Chlorophyll a Fluorescence at 295K

Figure 1B:
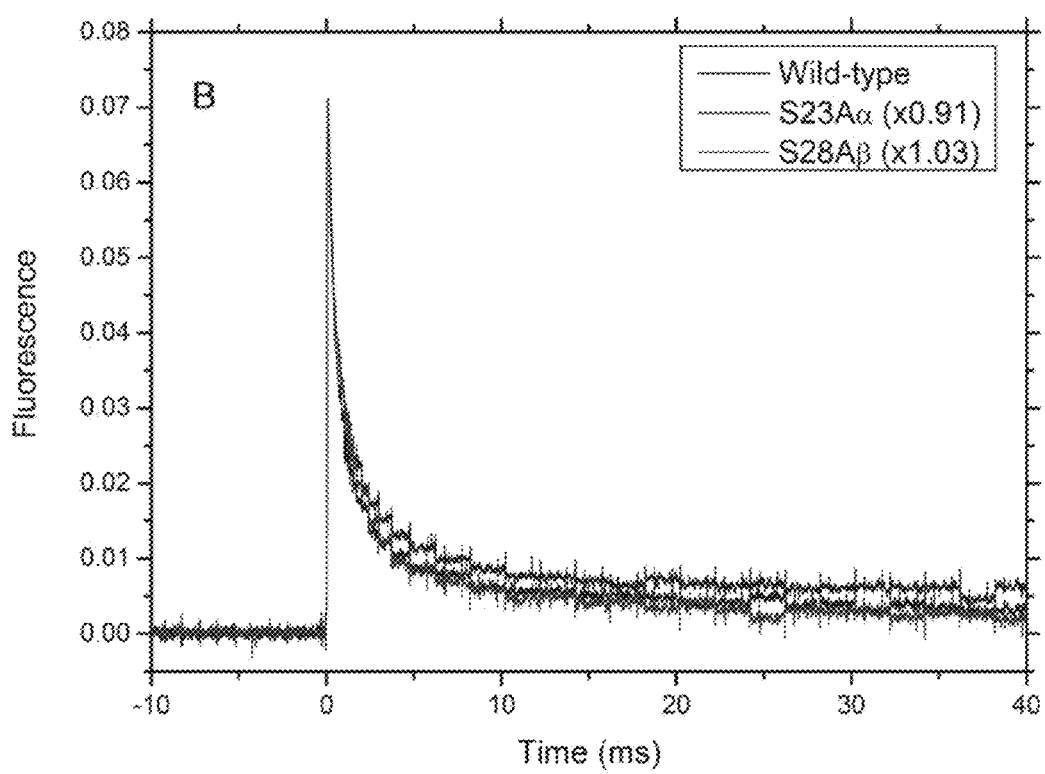
Figure 2A:
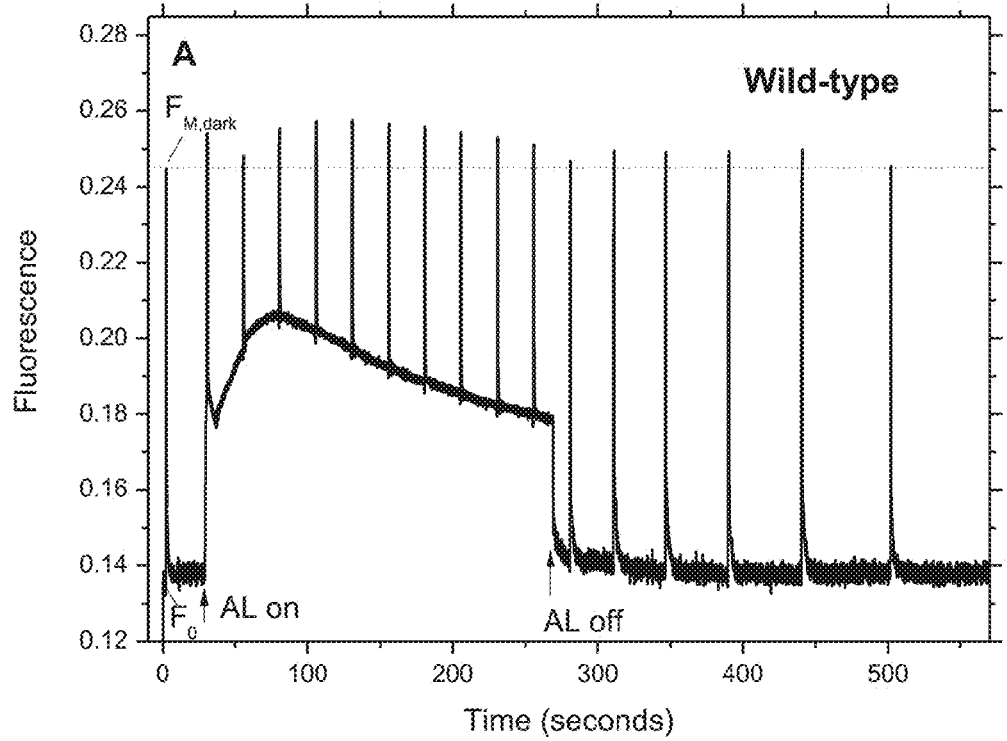
FIGS. 2A-2E show time-dependent flash-induced fluorescence yield of (FIG. 2A) wild-type, (FIG. 2B) A16FJ, (FIG. 2C) V32Fβ, (FIG. 2D) S23Aα and (FIG. 2E) S28Aβ mutant cells in the presence and absence of red actinic light. The intensity of the red actinic light was about 80-90 μE $m^{-2}s^{-1}$.
Figure 2B:
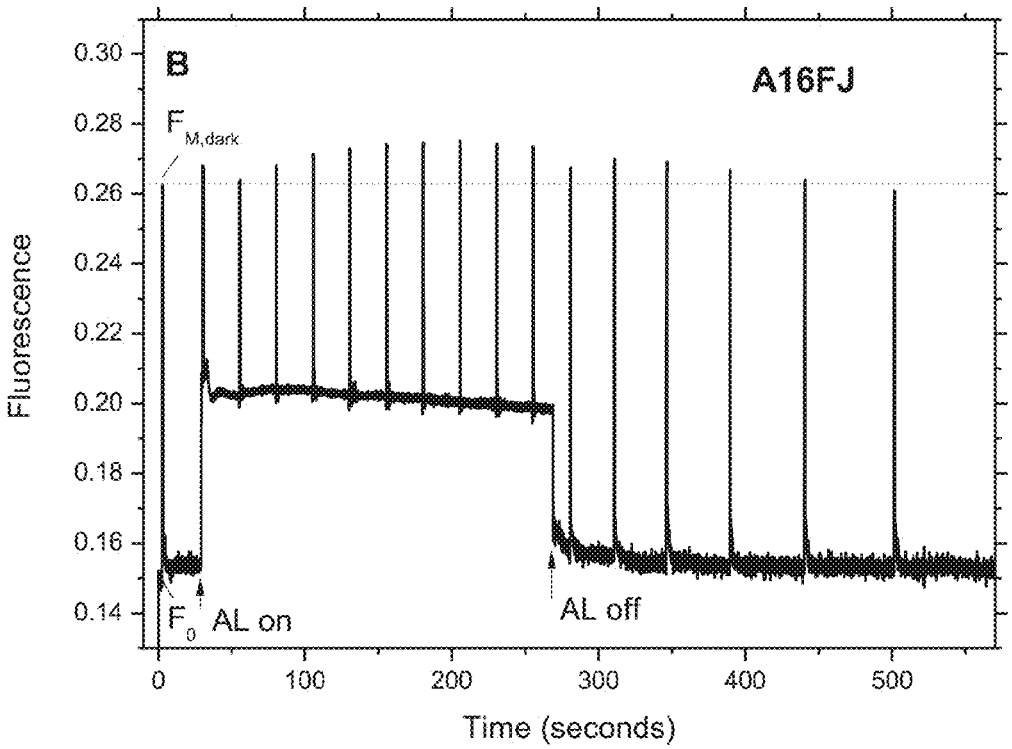
Figure 2C:
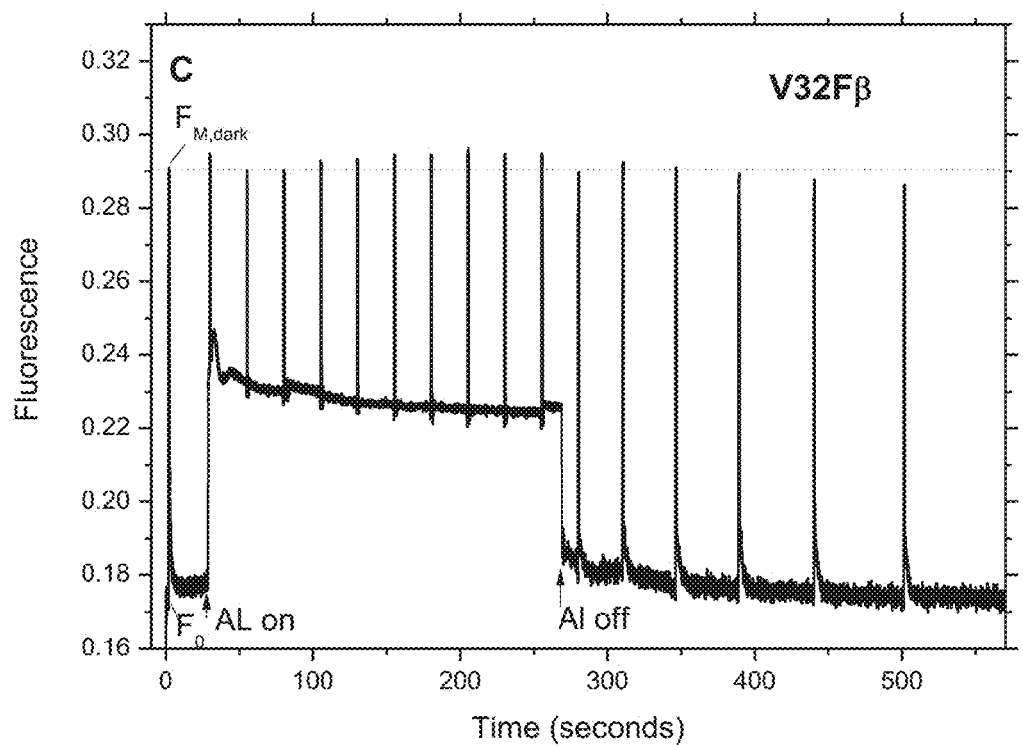
Figure 2D:
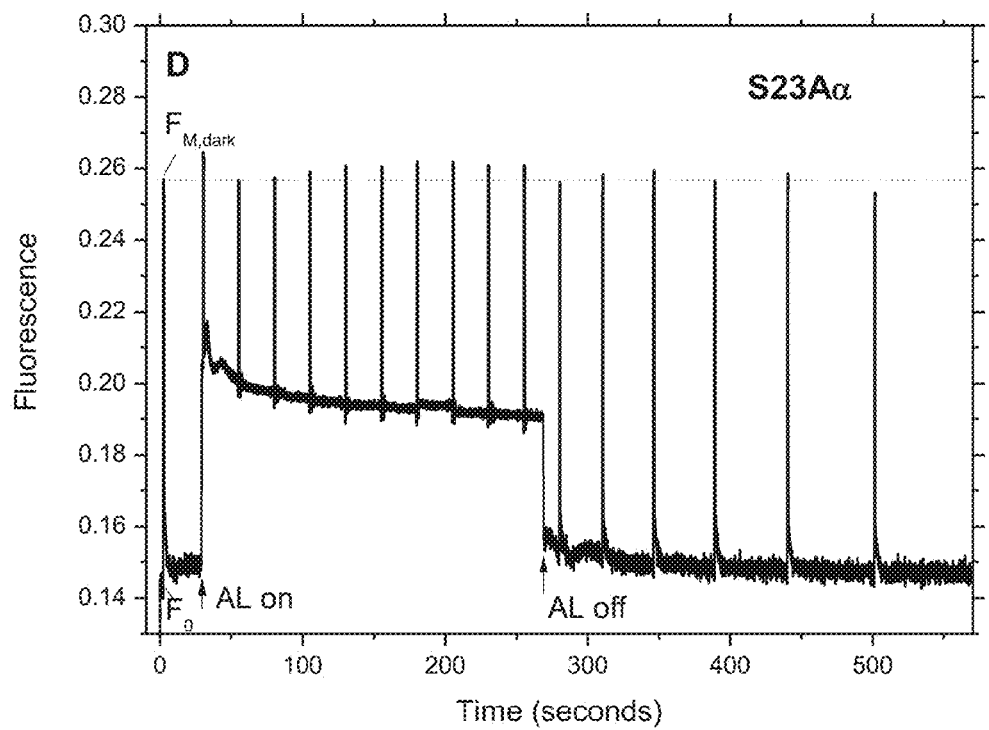
Figure 2E:
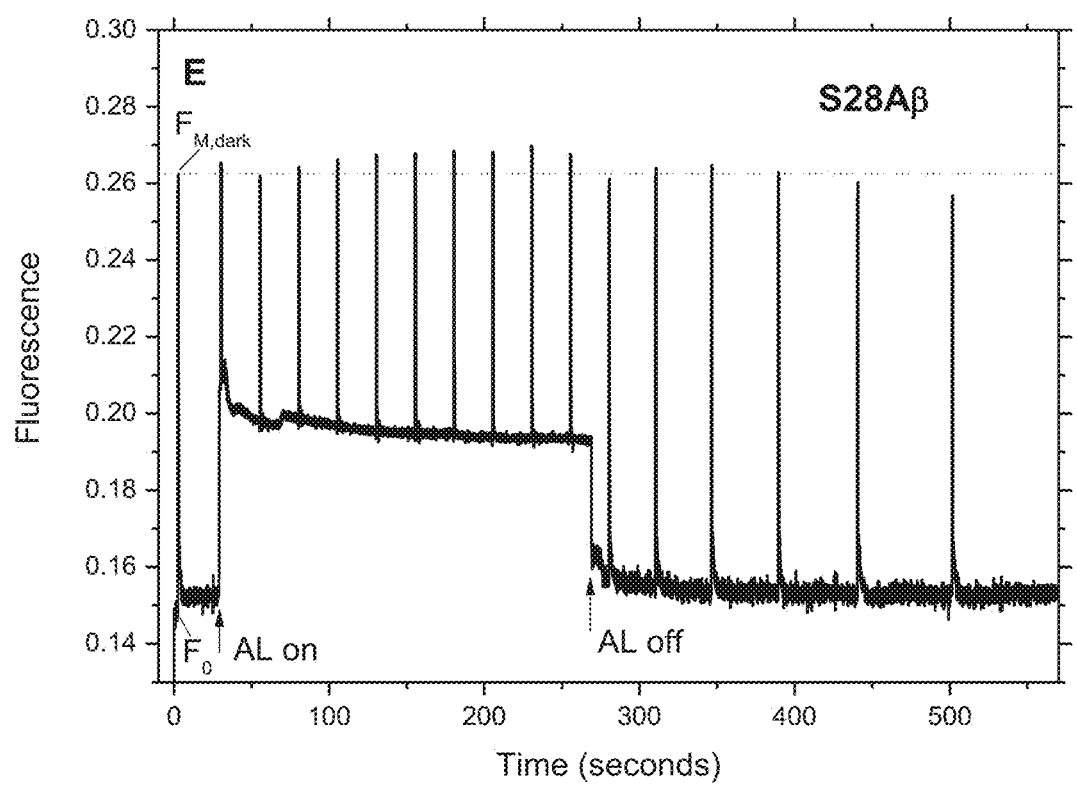

FIGS. 1A-1B show the induction and decay of $Q_A^-$ in response to a saturating single-turnover flash given to wild-type, A16FJ, V32Fβ, S23Aα and S28Aβ mutant cells in the absence of DCMU. Fluorescence decay in the absence of DCMU is mainly due to forward electron transfer from $Q_A^-$ to $Q_B$ and $Q_B^-$ [34]. Our results showed that the kinetics of electron transfer rate from $Q_A^-$ to $Q_B$ and $Q_B^-$ in these mutant cells was very similar to that in wild-type cells; except that there was a slight increase of a very slow phase in in the fluorescence decay kinetics of S23Aα cells, which could be attributed to the charge recombination between $Q_A^-$ and PSII electron donors. The other mutant cells listed in Table 1 all showed normal electron transfer from $Q_A^-$ to $Q_B$ and $Q_B^-$ like wild-type cells (data not shown). In addition, the kinetics of charge recombination between $Q_A^-$ and PSII electron donors in response to a saturating flash given to wild-type and mutant cells in the presence of DCMU were very similar as measured by chlorophyll a fluorescence (data not shown). These results indicate that the Mn cluster and $Q_A$ are generally intact in PSII of these mutant cells.

2.3 PSII Fluorescence Yield in the Presence and Absence of Red Actinic Light

FIGS. 2A-2E showed time-dependent flash-induced transients of PSII fluorescence yield for wild-type and mutant cells in the presence and absence of red actinic light. The $F_o$ values were slightly higher and the maximum PSII fluorescence yield ($F_v/F_{m,dark}$) was normal in dark-adapted mutant cells as compared to those of dark adapted wild-type cells. In addition, these mutant cells showed distinct time-dependent flash-induced transients of PSII fluorescence yield in the presence of red actinic light as compared to wild-type cells (See FIGS. 2A-2E). The steady state fluorescence yield ($F_s$) in wild-type cells typically showed an initial increase and then gradually decreased to a steady level during the actinic light illumination. In contrast, the $F_s$ levels in these mutant cells were relatively flat during the actinic light illumination. The results could be attributed to the subtle changes in fluorescence yield that accompany with state transitions during the actinic light illumination for these mutant cells as compared to wild-type cells ([35, 36] and references therein). In addition, the amplitude of maximum PSII fluorescence yield (Fm') after the red actinic light illumination (80-90 μE m$^{-2}$ s$^{-1}$) were comparable to the $F_{m,dark}$ in these mutant cells. Our results suggested that these mutant cells did not show any significant effect of photoinhibition under our experimental conditions.

2.4 Effects of Blue Light-Induced NPQ on Mutant Cells

Figure 3A:
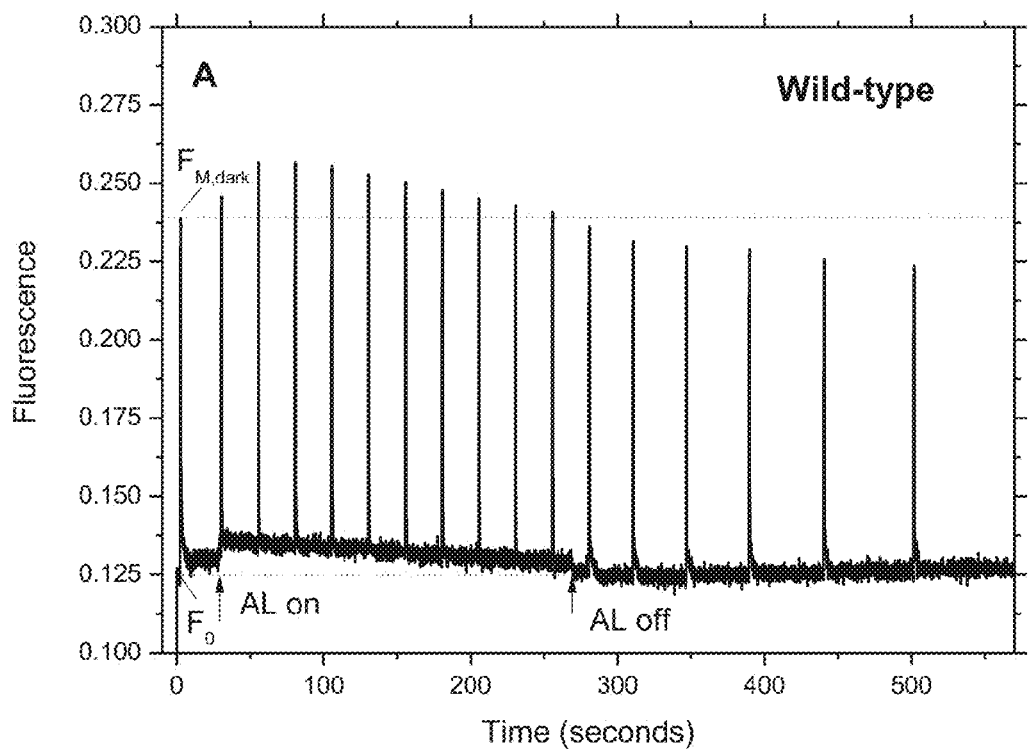
FIGS. 3A-3J show time-dependent flash-induced fluorescence yield of wild-type (FIG. 3A, FIG. 3F), A16FJ (FIG. 3B, FIG. 3G), V32Fβ (FIG. 3C, FIG. 3H), S23Aα (FIG. 3D, FIG. 3I) and S28Aβ (FIG. 3E, FIG. 3J) mutant cells in the presence and absence of blue actinic light. The intensity of the blue actinic light was (FIG. 3A) to (FIG. 3E) ~65 μE $m^{-2}$ $s^{-1}$ and (FIG. 3F) to (FIG. 3J) ~400 μE $m^{-2}$ $s^{-1}$. The other conditions were the same as in FIGS. 2A-2E.
Figure 3B:
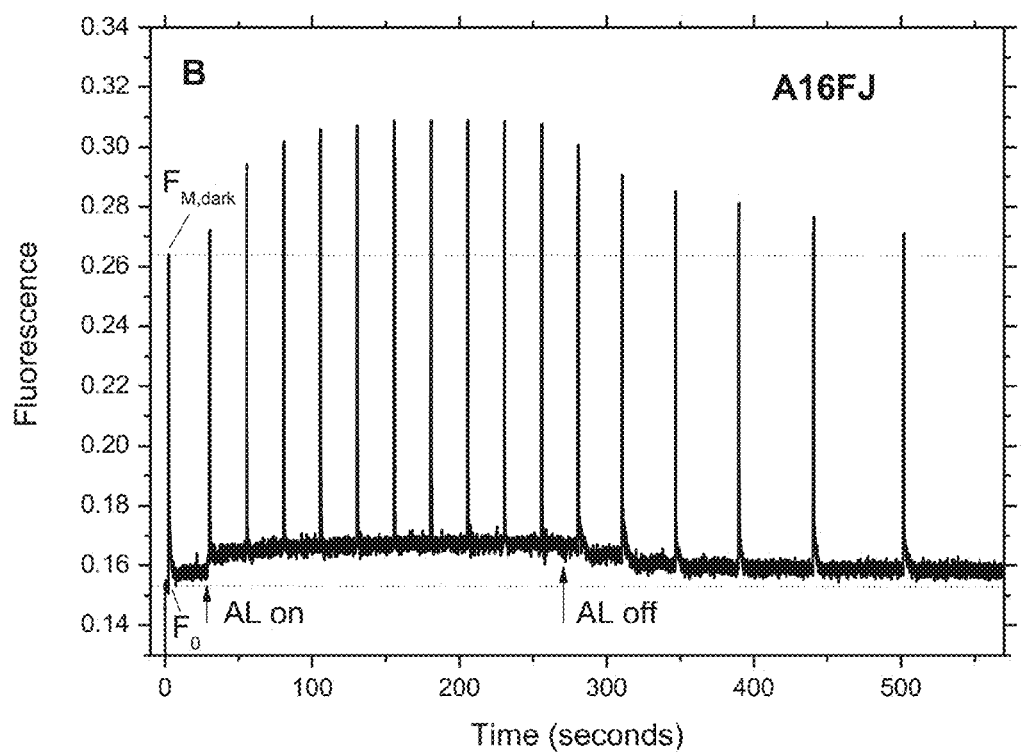
Figure 3C:
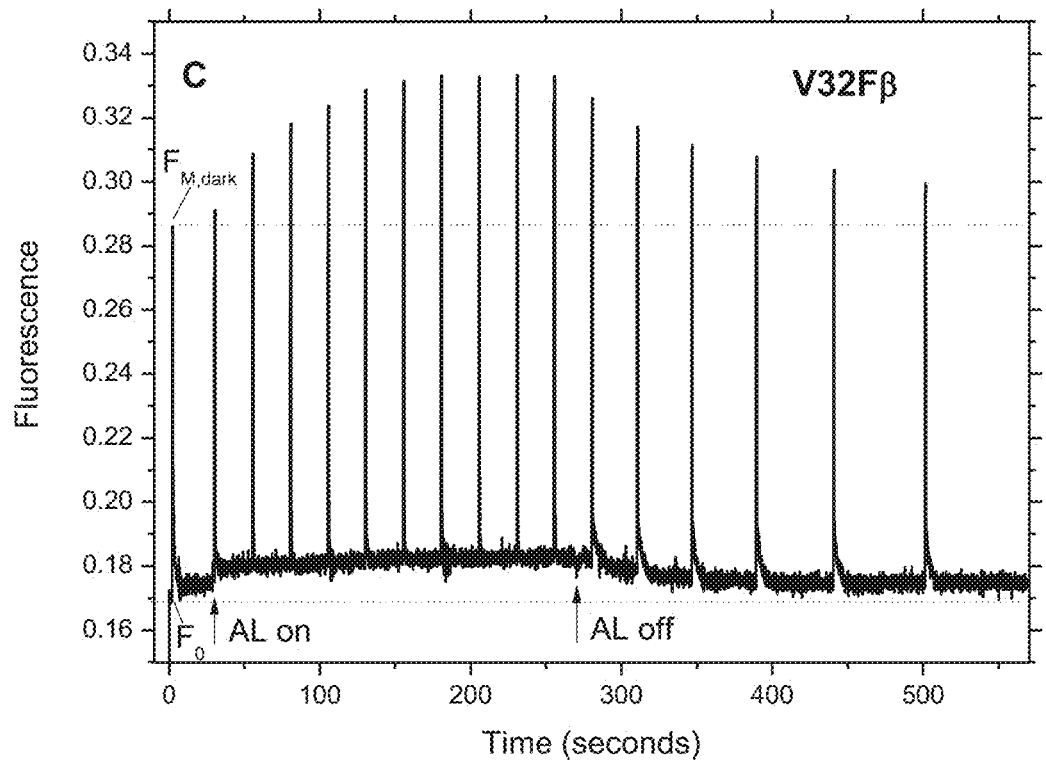
Figure 3D:
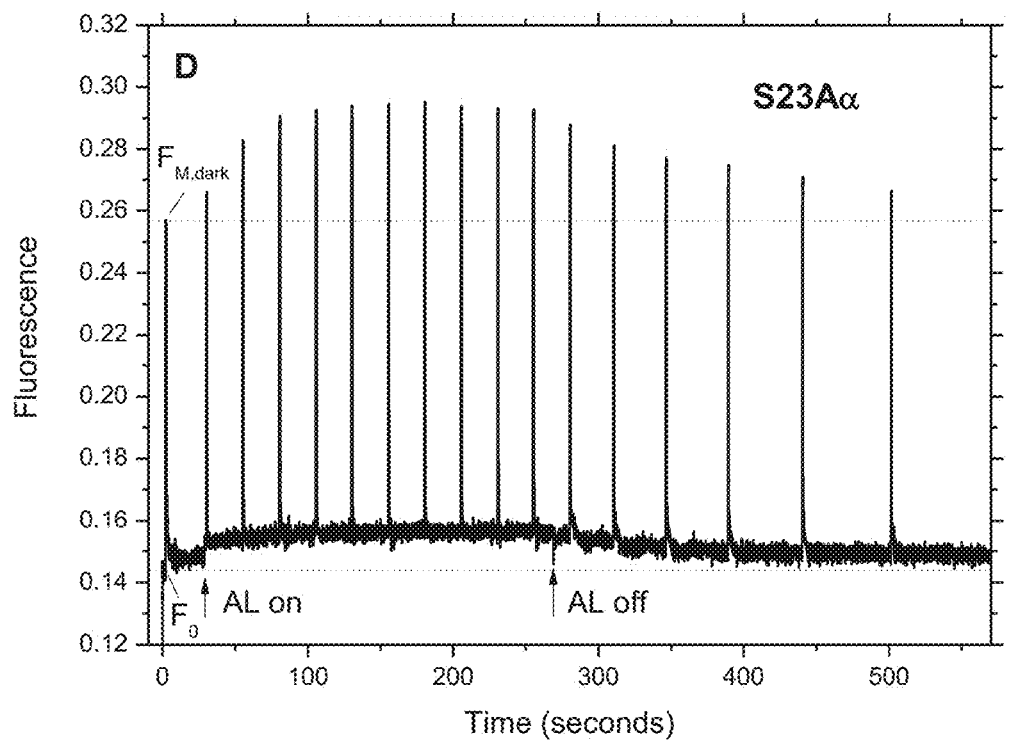
Figure 3E:
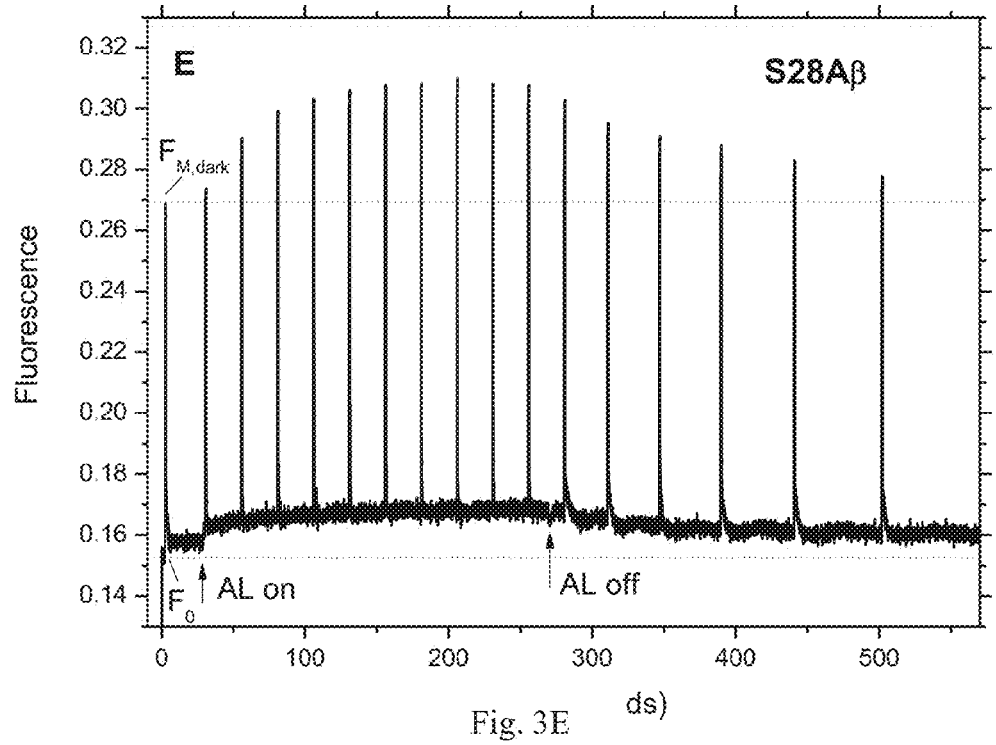
Figure 3F:
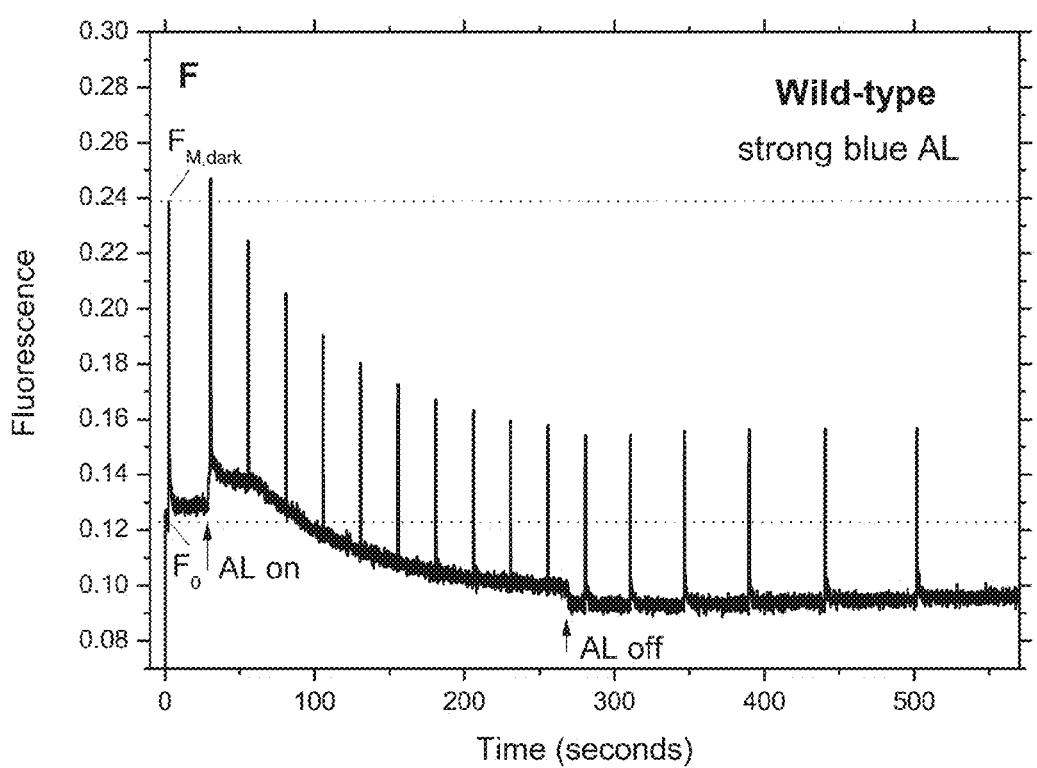
Figure 3G:
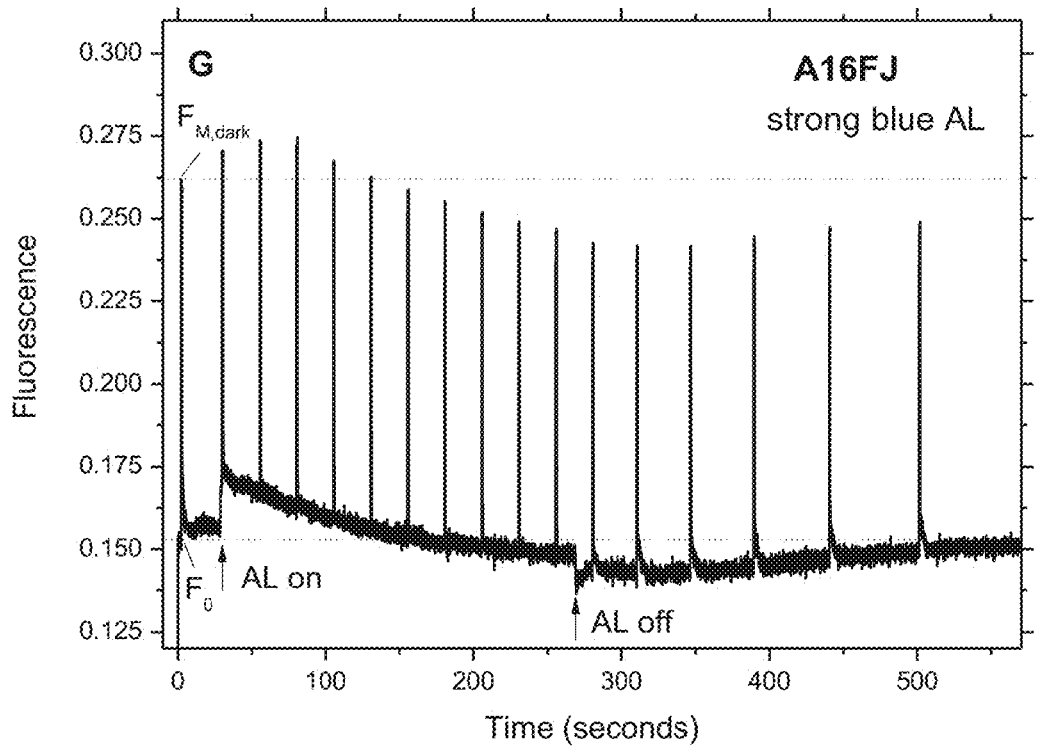
Figure 3H:
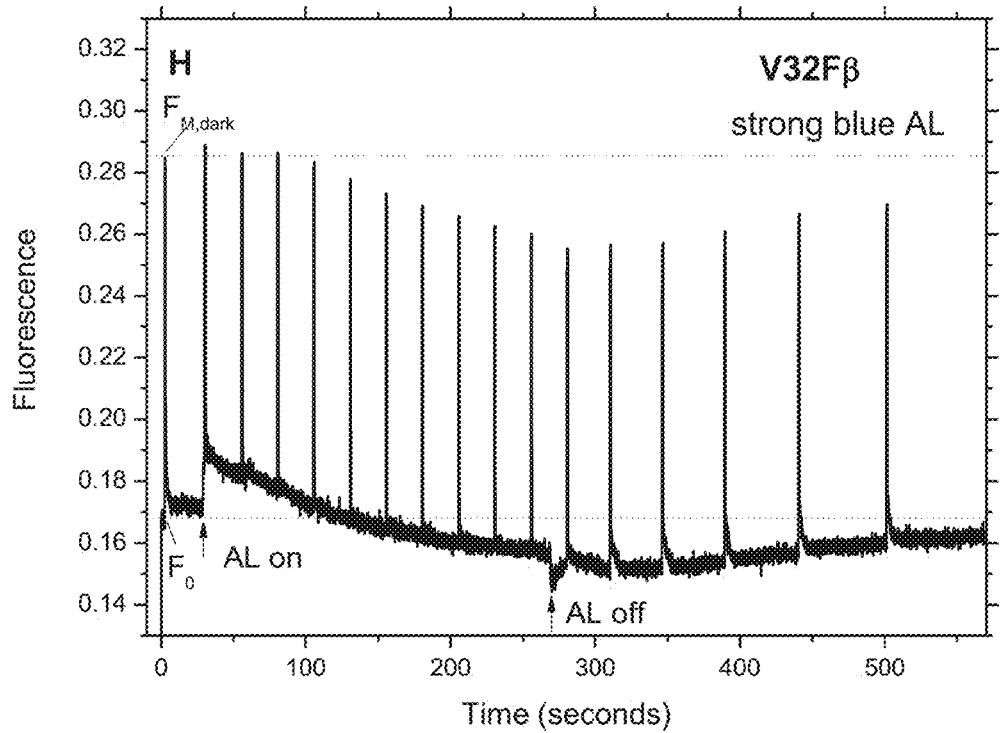
Figure 3I:
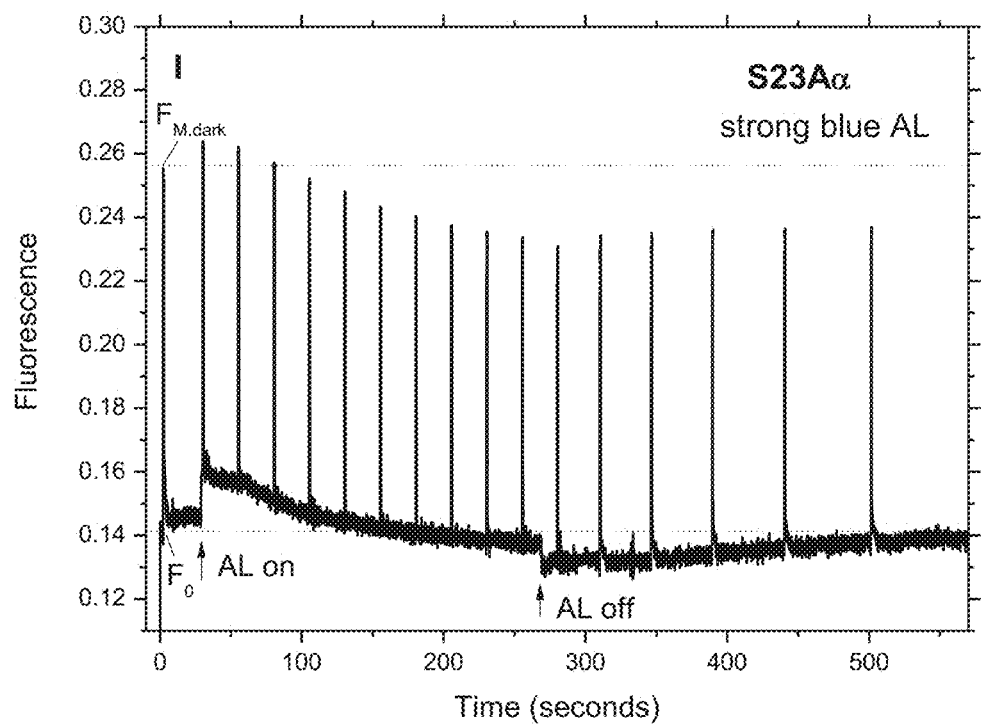
Figure 3J:
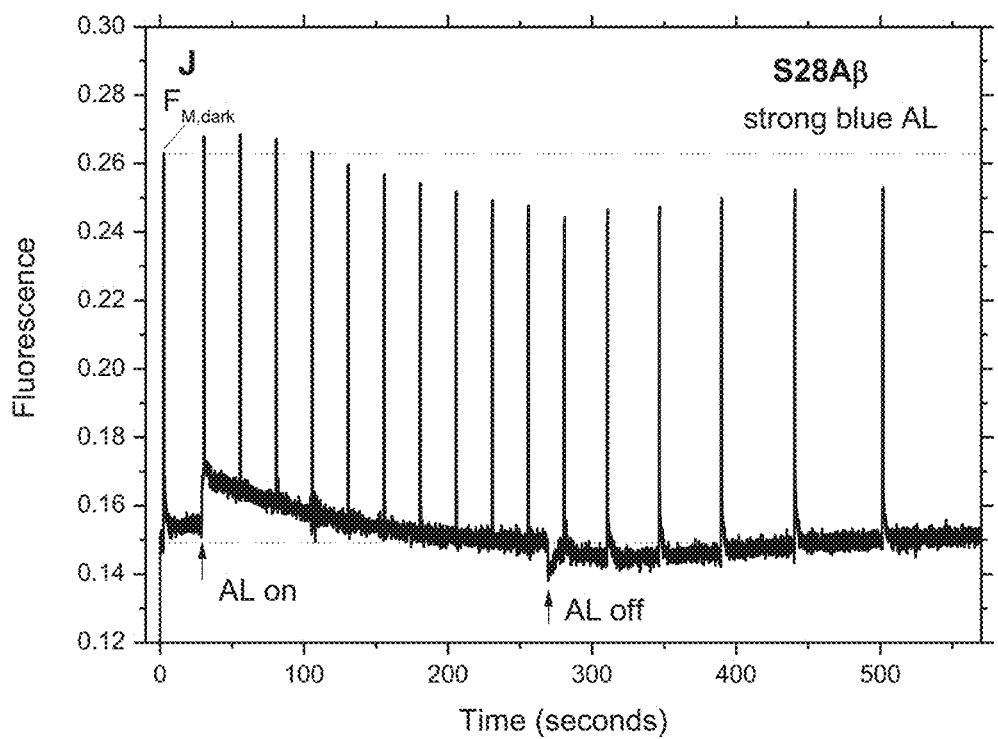

Most striking phenotype in these mutant cells was the inhibitory effects of blue light-induced NPQ in FIGS. 3B-3J as compared with FIG. 3A. When wild-type cells were illuminated with medium intensity (about 60 μE m$^{-2}$ s$^{-1}$) blue actinic light, their fluorescence yield showed a slight increase initially (possibly due to the state transition effect) and then decreased gradually due to the blue-light NPQ effect (see FIG. 3A). In contrast, when A16FJ, V32Fβ, S23Aα and S28Aβ mutant cells were illuminated with medium intensity (about 60 μE m$^{-2}$ s$^{-1}$) blue actinic light, their fluorescence yield showed an apparent increase to the higher level than wild-type cells (due to the state transition effect) but did not show any significant effect of blue-light induced NPQ (see FIG. 3B,C,D,E). When wild-type cells were illuminated with 400 μμE m$^{-2}$ s$^{-1}$ blue actinic light, a strong quenching in their fluorescence yields was induced and the steady-state fluorescence ($F_s$) levels dropped below the $F_o$ level during the blue actinic light illumination (FIG. 3F). Once blue actinic light was turned off, the $F_m'$ and $F_o'$ recovered slowly back to the initial level in the dark. In contrast, these mutant cells showed only a slight decrease in fluorescence yield under the same experimental conditions (FIGS. 3G-3J). In addition, when the blue actinic light was turned off, the recovery of NPQ in these mutant cells was almost complete within 6 minutes, whereas the recovery of NPQ in wild-type cells was significantly slower. Our results indicated that the effects of blue-light-induced NPQ were severely inhibited and the dark-recovery of NPQ was significantly accelerated in these mutant cells. A16RJ, A20FJ and S28Vβ mutant cells also showed severe inhibition on blue-light-induced NPQ effect as these mutant cells mentioned above (data not shown). In contrast, the other mutant cells (A16SJ, A16LJ, and G19FJ) in Table 1 showed normal blue-light-induced NPQ effects as wild-type cells.

2.5 Western Blot Analysis

Figure 4:
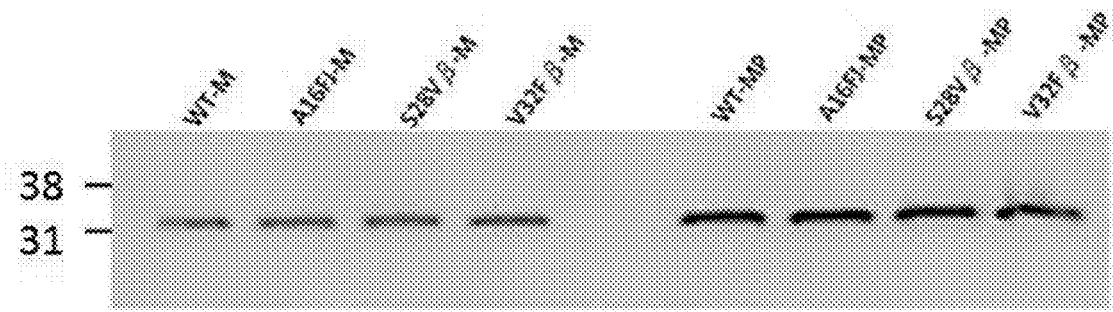
FIG. 4 shows western blot analysis on the OCP content of wild-type and mutant thylakoid membranes.
Figure 5A:
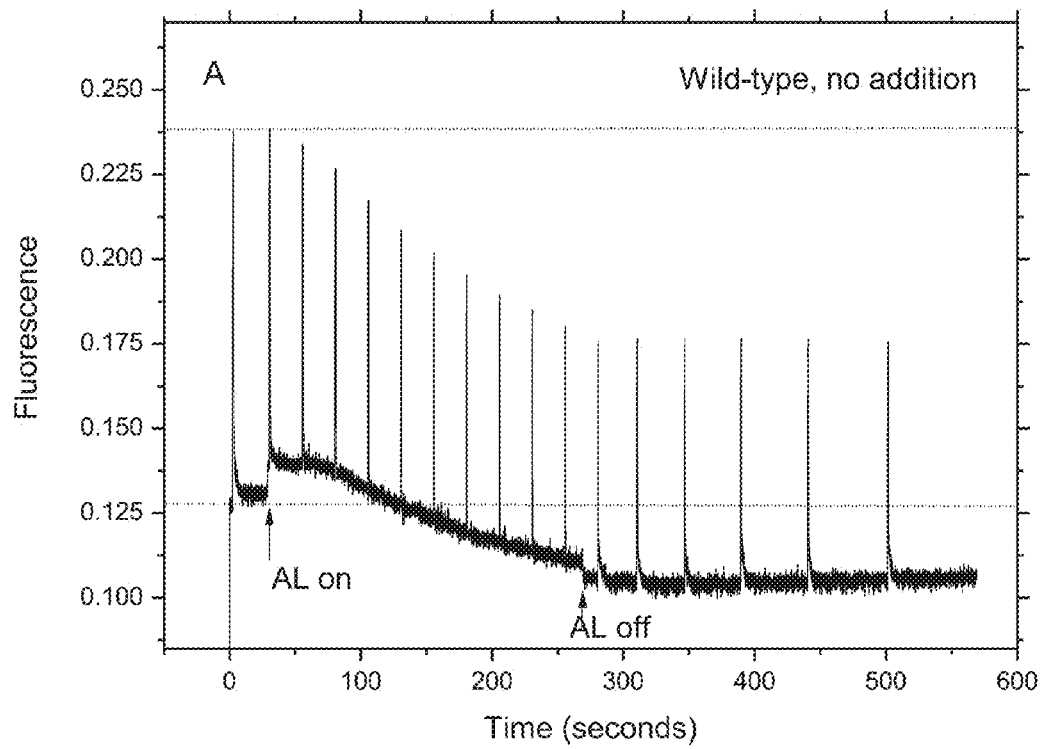
FIGS. 5A-5D show the effect of DCMU, DBMIB and red light on time-dependent flash-induced fluorescence yield of wild-type cells in the presence and absence of strong blue actinic light.
Figure 5B:
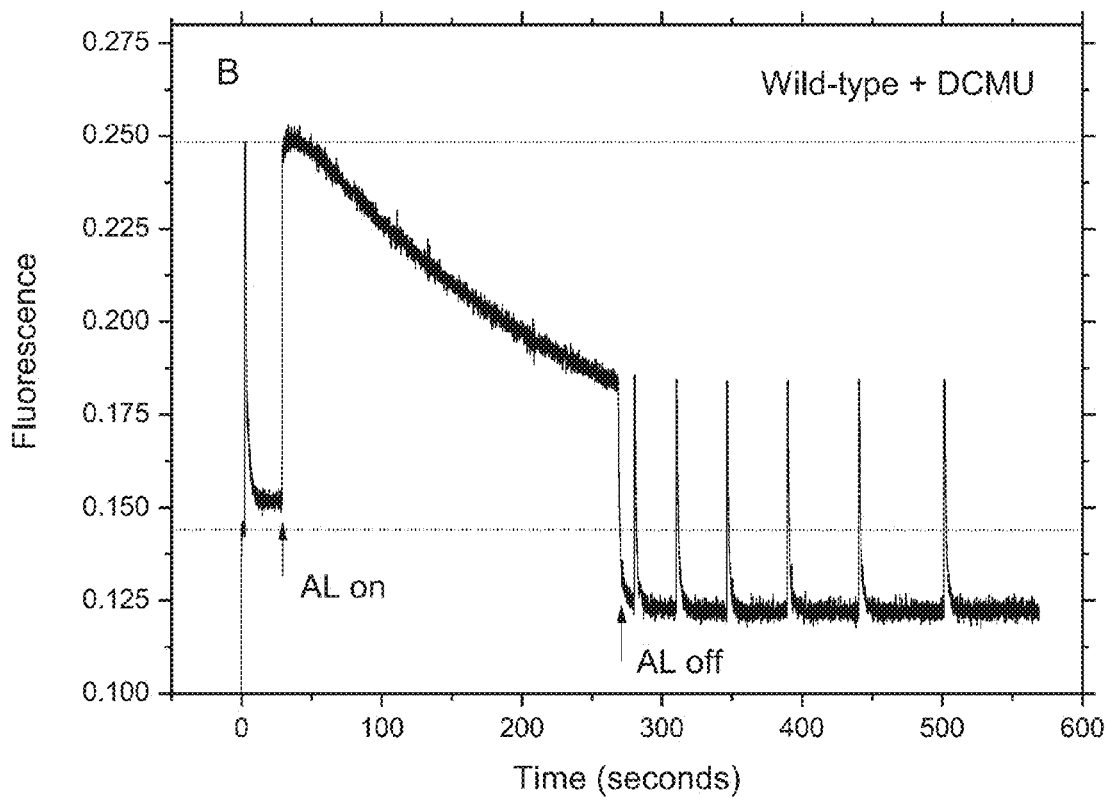
Figure 5C:
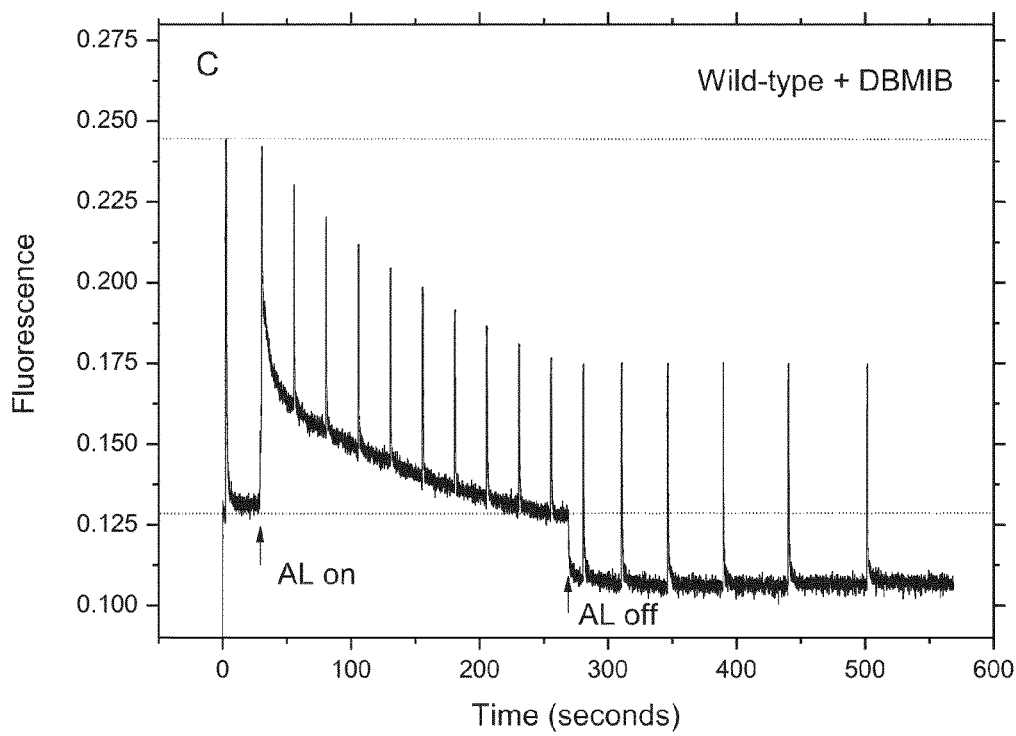
Figure 5D:
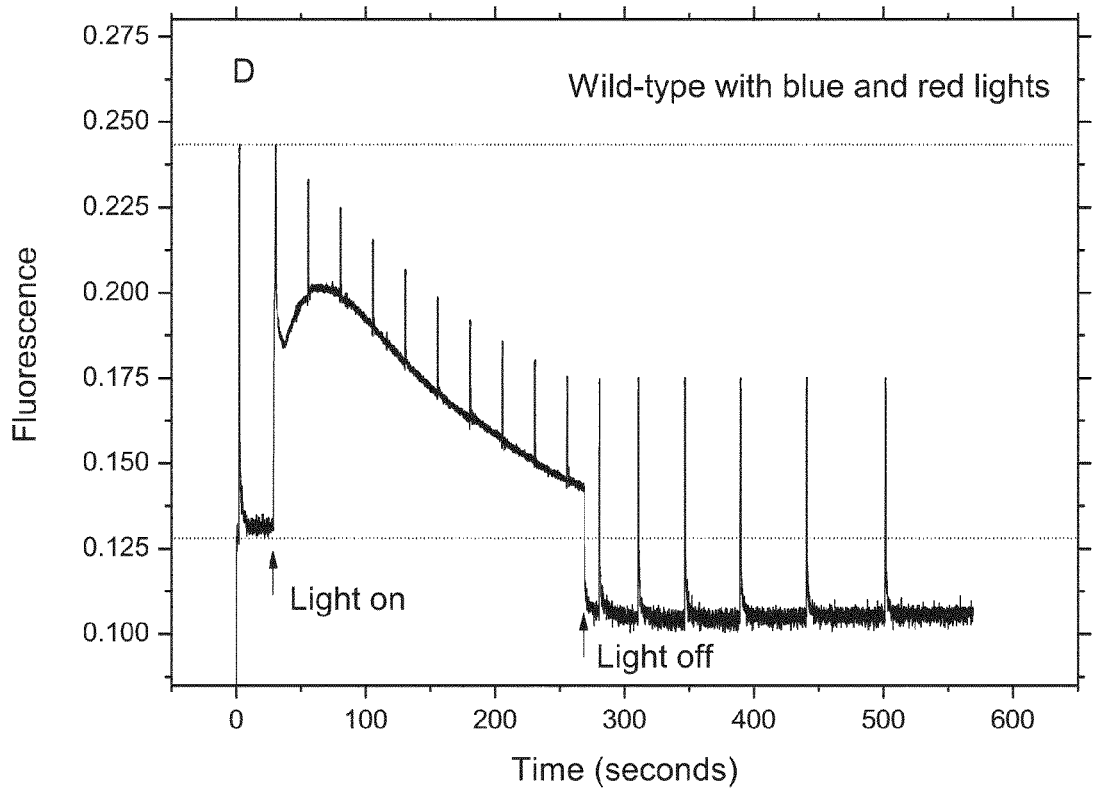

To determine whether these mutant cells have normal amount of OCP as wild-type cells, we perform western blot analysis on the OCP content of wild-type and mutant thylakoid membranes in FIG. 4. Our results showed that A16FJ, V32Fβ and S28Vβ mutant thylakoid membranes still contained normal amount of OCP as wild-type cells. Therefore, our results conclude that the inhibitory effect of OCP-induced NPQ in these mutant cells was not due to the lack of OCP.

2.6 Effects of DCMU and DBMIB on OCP-Mediated NPQ in Synechocystis 6803

FIGS. 5A-5D showed the OCP-mediated NPQ in the presence of DCMU (panel A), DBMIB (panel B), no addition (panel C) with blue actinic light, and no addition with blue and red actinic lights (panel D) in wild-type cells of Synechocystis 6803. The presence of DCMU during actinic light illumination will induce the oxidation of the PQ pool in Synechocystis 6803 cells. In contrast, the presence of DBMIB will make the PQ pool of Synechocystis 6803 cells more reduced during illumination (see FIG. 5B). In addition, the illumination of blue-plus-red actinic lights (see FIG. 5D) will also make the PQ pool of Synechocystis 6803 cells more reduced than the illumination of blue actinic light alone (see FIG. 5C). Our results in FIGS. 5A-5D showed that DCMU and DBMIB treatments and the illumination of blue-plus-red actinic light did not significantly alter the OCP-mediated photoprotection in wild-type cells. Our results suggested that the changes in the redox state of PQ pool did not significantly alter the OCP-mediated photoprotection in *Synechocystis* 6803 cells.

2.7 Photosynthetic Growth Rate and Biomass Analysis of Mutant Cells

Figure 6:
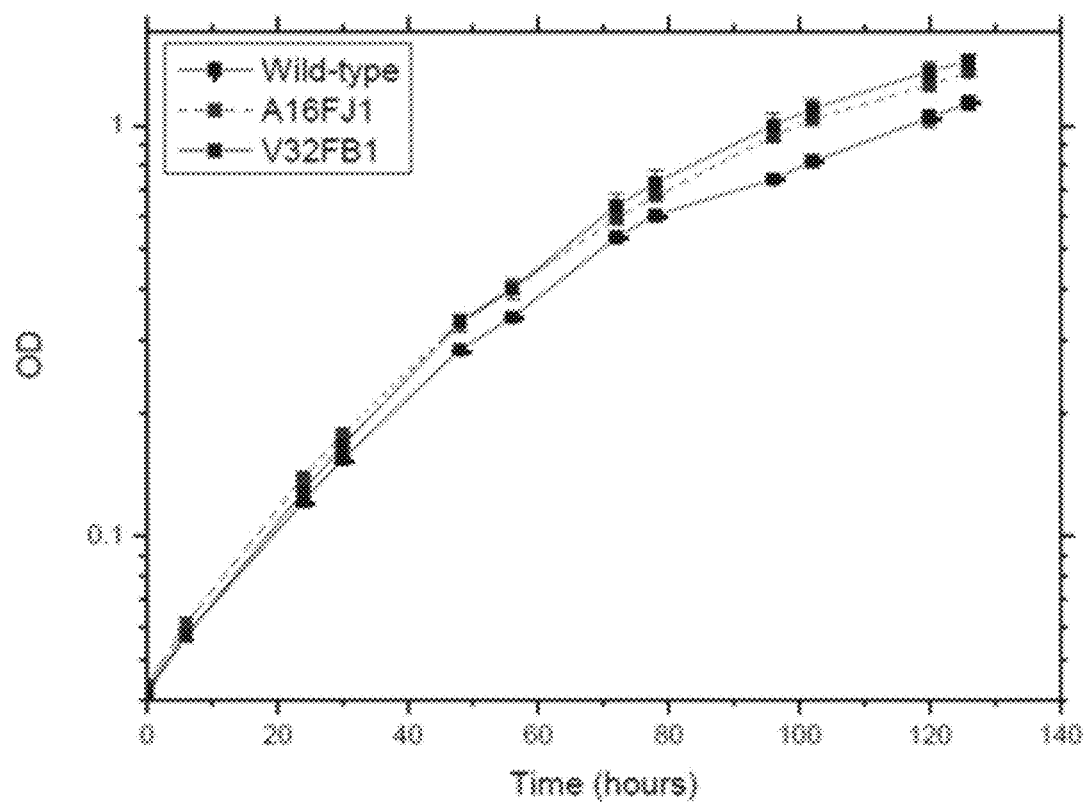
FIG. 6 shows the photosynthetic growth curves of wild-type and mutant cells at 30° C. in ambient air and 30 μmol μE $m^{-2}$ $s^{-1}$ from fluorescent lights. Error bars indicate the standard deviation of two biological replicates. When error bars cannot be seen, the error was smaller than the size of the symbol.

FIG. 6 showed the photosynthetic growth curve of wild-type and mutant cells. Our results showed that A16FJ and V32Fβ mutant cells showed significantly higher photosynthetic growth rate compared to wild-type cells. The doubling time of photosynthetic growth rates in wild-type, A16FJ and V32Fβ mutant cells were 17.2±0.2, 15.7±0.1, 15.7±0.2 (see Table 2). In addition, the biomass concentration in 5 day culture of A16FJ and V32Fβ mutant cells (0.280±0.020 and 0.303±0.017, respectively) was significantly higher than that of wild-type cells (0.213±0.011 mg/ml) (see Table 2). Therefore, our results showed that photosynthetic growth rates and biomass production were significantly enhanced in A16FJ and V32Fβ mutant cells as compared to wild-type cells.

TABLE 2

Photosynthetic growth rates and biomass production in wild-types and mutant cells.

| Strain | Doubling time (hour) | Biomass concentration (mg/ml) |
|---|---|---|
| Wild-type | 17.2 ± 0.2 | 0.213 ± 0.011 |
| A16FJ | 15.7 ± 0.1 | 0.280 ± 0.020 |
| V32Fβ | 15.7 ± 0.2 | 0.303 ± 0.017 |

Cultures were grown under at 30° C. in ambient air and 30 μmol μE m$^{-2}$ s$^{-1}$ from white fluorescent lights. Photosynthetic growth rates were measured for cells at exponential growth. Biomass concentrations of cultures were measured after about 126 hour growth. Error bars indicate the standard errors of three independent experiments.

3. Discussion 3.1 Mutations on Cytb559 and PsbJ Alter Blue Light-Induced NPQ in Cyanobacteria Our results showed that blue-light-induced NPQ was significantly inhibited in several Cytb$_{559}$ and PsbJ mutant cells. Previous studies have demonstrated in vitro that the activated red form of OCP interacts with the phycobilisome and induces NPQ in cyanobacteria. The interaction site for the OCP was proposed to be on one of the central allophycocyanin (APC) disks of the base cylinders [16, 17]. In addition, our western blot results further showed that the amount of OCP in A16FJ, V32Fβ and S28Vα mutant thylakoid membranes were similar to wild-type thylakoid membranes. Therefore, the inhibition of OCP-induced NPQ in these mutant cells was not due to the lack of OCP. Furthermore, DCMU, DBMIB and blue-plus-red actinic light treatments did not significantly alter OCP-induced NPQ in *Synechocystis* 6803. Our results is consistent with results from previous studies which suggest that OCP-induced NPQ in cyanobacteria is not affected by changes in transthylakoidal pH or the redox state of the PQ pool but dependent on light irradiance and quality [10].

In addition, several mutant cells, e.g. A16FJ, V32Fβ, G19FJ, A20FJ, in Table 1 showed normal photosynthetic water oxidation and kinetic of electron transfer from $Q_A$ to $Q_B$ and $Q_B^-$. Because these residues are constructed near the opening of the proposed $Q_C$ transfer channel, the replacement of these residues with bulky phenylalanine is expected to hinder or block the diffusion of the PQ molecule through the channel. However, we did not see such effects in these mutant cells. Therefore, our results were not consistent with the proposal that the $Q_C$-site or the $Q_C$ transfer channel may play a significant role in exchange of PQ on the $Q_B$ site from the pool in cyanobacteria [3].

3.2 The Implication on the Involvement of Cyt b559 and PsbJ in Blue Light-Induced NPQ Mechanism The cytoplasmic side of Cyt $b_{559}$ is located within the predicted contact sites in PSII for the APC core complex of the phycobilisome [38]. In addition, our previous study showed that the R7Lα and R17Lβ mutation on the cytoplasmic side of Cyt $b_{559}$ has a significant inhibitory effect on OCP-induced NPQ and its dark-recovery [32]. Therefore, we propose that the mutations on Cyt $b_{559}$ and PsbJ may affect OCP-mediated NPQ in cyanobacteria presumably through altering the interaction between the APC core complex and the OCP. Our results also suggested that the cytoplasmic side of Cyt $b_{559}$ and PsbJ might contribute or stabilize the docking site in PSII for the APC core complex and the OCP. This proposal is also consistent with a recent study on the structural binding site of the OCP by using a combination of native electrospray mass spectrometry and protein cross-linking [39].

3.3 The Application of These Mutant Cells for Bioenergy Production.

A16FJ and V32Fβ mutant cells showed significantly higher photosynthetic growth rates (about 1.1 folded) and increased biomass accumulation (about 30-40% higher) than wild-type cells under our normal growth conditions. Because these mutant cells showed severe inhibition on OCP-induced NPQ mechanism, therefore the above effects can be attributed to the decrease of wasteful energy dissipation from their phycobilisomes and thereby improve their photosynthesis efficiency as compared to wild-type cells. The improved photosynthesis and growth characteristics of these mutant cells may have the practical applications to enhance the biomass and biofuel production in cyanobacteria [40-42]. Our FT-IR analysis showed that lipid, protein and carbohydrate content were higher for A16FJ and V32Fb mutant cells as compared with WT cells under our normal growth conditions.

4. Conclusions

Our results showed that several Synechocystis PCC6803 mutant cells with point mutations on Cyt $b_{559}$ and PsbJ showed enhanced effects of state transitions under medium blue light and weakened effects of blue-light-induced NPQ under strong blue-light conditions. Our results suggest that Cyt b559 and PsbJ of PSII modulate state transitions and blue-light-induced NPQ in cyanobacteria. In addition, photosynthetic growth rate and biomass production were greater for some mutant cells than WT cells under our normal growth conditions. These mutant cells may have practical applications in increasing biomass yield and bioenergy production of cyanobacteria.

SEQUENCE INFORMATION

A wild type cytochrome b559 α polypeptide
(SEQ ID NO: 1)
SGTTGERPFSDIVTSIRYWVIH<u>S</u>ITIPMLFIAGWLFVSTGLAYDAFGTP
RPDEYFTQTRQELPILQERYDINQEIQEFNQ A wild type cytochrome b559 β polypeptide
(SEQ ID NO: 2)
ATQNPNQPVTYPIFTVRWLAVHTLAVP<u>S</u>VFF<u>V</u>GAIAAMQFIQR A wild type cytochrome PsbJ polypeptide
(SEQ ID NO: 3)
MFAEGRIPLWVVGVV<u>A</u>GIG<u>A</u>IGVLGLFFYGAYAGLGSSM

SEQUENCE INFORMATION

A mutant cytochrome b559 α polypeptide
(S23Aα)
(SEQ ID NO: 4)
SGTTGERPFSDIVTSIRYWVIHAITIPMLFIAGWLFVSTGLAYDAFGTP
RPDEYFTQTRQELPILQERYDINQEIQEFNQ A mutant cytochrome b559 β polypeptide
(S28Aβ)
(SEQ ID NO: 5)
ATQNPNQPVTYPIFTVRWLAVHTLAVPAVFFVGAIAAMQFIQR A mutant cytochrome b559 β polypeptide
(S28Vβ)
(SEQ ID NO: 6)
ATQNPNQPVTYPIFTVRWLAVHTLAVPVVFFVGAIAAMQFIQR A mutant cytochrome b559 β polypeptide
(V32Fβ)
(SEQ ID NO: 7)
ATQNPNQPVTYPIFTVRWLAVHTLAVPSVFFFGAIAAMQFIQR A mutant cytochrome PsbJ polypeptide
(A16FJ)
(SEQ ID NO: 8)
MFAEGRIPLWVVGVVFGIGAIGVLGLFFYGAYAGLGSSM A mutant cytochrome PsbJ polypeptide
(A16RJ)
(SEQ ID NO: 9)
MFAEGRIPLWVVGVVRGIGAIGVLGLFFYGAYAGLGSSM A mutant cytochrome PsbJ polypeptide
(A20FJ)
(SEQ ID NO: 10)
MFAEGRIPLWVVGVVAGIGFIGVLGLFFYGAYAGLGSSM

REFERENCES

1. D. J. Vinyard, G. M. Ananyev, G. C. Dismukes, Photosystem II: the reaction center of oxygenic photosynthesis, Annu. Rev. Biochem. 82 (2013) 577-606.
2. J. Barber, Photosystem II: the water-splitting enzyme of photosynthesis, Cold Spring Harb Symp Quant Biol. 77 (2012) 295-307.
3. Y. Umena, K. Kawakami, J.-R. Shen, N. Kamiya, Crystal structure of oxygen-evolving photosystem II at a resolution of 1.9 Å, Nature 473 (2011) 55-60.
4. A. Guskov, J. Kern, A. Gabdulkhakov, M. Broser, A. Zouni, W. Saenger, Cyanobacterial photosystem II at 2.9-Å resolution and the role of quinones, lipids, channels and chloride, Nature Struct. Biol. & Mol. Biol. 16 (2009) 334-342.
5. Tyystjärvi E, Photoinhibition of Photosystem II, Int Rev Cell Mol Biol. 300 (2013) 243-303.
6. K. K. Niyogi, T. B. Truong, Evolution of flexible non-photochemical quenching mechanisms that regulate light harvesting in oxygenic photosynthesis, Curr. Opin. Plant Biol. 3 (2013) 307-14.
7. P. Horton, Optimization of light harvesting and photoprotection: molecular mechanisms and physiological consequences, Philos Trans R Soc Lond B Biol Sci. 367 (2012) 3455-3465.
8. D. Kirilovsky, C. A. Kerfeld, The orange carotenoid protein in photoprotection of photosystem II in cyanobacteria, Biochim. Biophys. Acta, Bioenerg. 1817 (2012) 158-166.
9. D. Kirilovsky, C. A. Kerfeld, The orange Carotenoid protein: a blue-green light photoactive protein, Photochem. Photobiol. Sci. 12 (2013) 1135-1143.
10. A. Wilson, G. Ajlani, J. -M. Verbavatz, I. Vass, C. A. Kerfeld, D. Kirilovsky, A soluble carotenoid protein involved in phycobilisome-related energy dissipation in cyanobacteria, Plant Cell 18 (2006) 992-1007.
11. C. Boulay , L. Abasova, C. Six, I. Vass, D. Kirilovsky, Occurrence and function of the orange carotenoid protein in photoprotective mechanisms in various cyanobacteria, Biochim. Biophys. Acta, Bioenerg. 1777 (2008) 1344-1354.
12. A. Wilson, D. Kirilovsky, In vitro reconstitution of the cyanobacterial photoprotective mechanism mediated by the orange carotenoid protein in Synechocystis PCC 6803, Plant Cell 23 (2011) 2631-2643.
13. C. Boulaya, A. Wilsona, S. D'Haenec, D. Kirilovsky, Identification of a protein required for recovery of full antenna capacity in OCP-related photoprotective mechanism in cyanobacteria, PNAS 107 (2010) 11620-11625.
14. D. Jallet, M. Gwizdala, D. Kirilovsky, ApcD, ApcF and ApcE are not required for the Orange Carotenoid Protein related phycobilisome fluorescence quenching in the cyanobacterium *Synechocystis* PCC 6803, Biochim. Biophys. Acta, Bioenerg. 1817 (2012) 1418-1427.
15. I. N. Stadnichuk, M. F. Yanyushin, E. G. Maksimov, E. P. Lukashev, S. K. Zharmukhamedov, I. V. Elanskaya, V. Z. Paschenko, Site of non-photochemical quenching of the phycobilisome by orange carotenoid protein in the cyanobacterium *Synechocystis* sp. PCC 6803, Biochim. Biophys. Acta, Bioenerg. 1817 (2012) 1436-1445.
16. Tian L, van Stokkum I H, Koehorst R B, Jongerius A, Kirilovsky D, van Amerongen H., Site, rate, and mechanism of photoprotective quenching in cyanobacteria, J Am Chem Soc. 133 (2011) 18304-18311.
17. Leverenz R L, Jallet D, Li M D, Mathies R A, Kirilovsky D, Kerfeld C A. Structural and Functional Modularity of the Orange Carotenoid Protein: Distinct Roles for the N- and C-Terminal Domains in Cyanobacterial Photoprotection, Plant Cell 26 (2014) 426-437.
18. Jallet D, Thurotte A, Leverenz R L, Perreau F, Kerfeld C A, Kirilovsky D. Specificity of the cyanobacterial Orange Carotenoid Protein: Influences of OCP and phycobilisome structures, Plant Physiol. (2013).
19. F. Müh, C. Glöckner, J. Hellmich, A. Zouni, Light-induced quinone reduction in photosystem II, Biochim. Biophys. Acta, Bioenerg. 1817 (2012) 44-65.
20. O. Kaminskaya, V. A. Shuvalov, G. Renger, Evidence for a novel quinone binding site in the photosystem II complex that regulate the redox potential of cytochrome $b_{559}$, Biochemistry 46 (2007) 1091-1105.
21. O. Kaminskaya, V. A. Shuvalov, G. Renger, Two reaction pathways for transformation of high potential cytochrome $b_{559}$ of PS II into the intermediate potential form, Biochim. Biophys. Acta, Bioenerg. 1767 (2007) 550-558.
22. O. Kaminskaya, V. A. Shuvalov, Biphasic reduction of cytochrome b559 by plastoquinol in photosystem II membrane fragments, Evidence for two types of cytochrome b559/plastoquinone redox equilibria, Biochim. Biophys. Acta, Bioenerg. 1827 (2013) 471-483.
23. P. Pospisil, Enzymatic function of cytochrome $b_{559}$ in photosystem II, J. Photochem. Photobiol., B. 104 (2011) 341-347.
24. K. E. Shinopoulos, G. W. Brudvig, Cytochrome $b_{559}$ and cyclic electron transfer within photosystem II, Biochim. Biophys. Acta, Bioenerg. 1817 (2011) 66-75.

25. J. Kruk, K. Strzalka, Dark reoxidation of the plastoquinone-pool is mediated by the low-potential form of cytochrome b-559 in spinach thylakoids, Photosynth. Res. 62 (1999) 273-279.
26. J. Kruk, K. Strzalka, Redox changes of cytochrome $b_{559}$ in the presence of plastoquinone, J. Biol. Chem. 276 (2001) 86-91.
27. N. Bondarava, L. De Pascalis, S. Al-Babili, C. Goussias, J. R. Golecki, P. Beyer, R. Bock, A. Krieger-Liszkay, Evidence that cytochrome $b_{559}$ mediates the oxidization of reduced plastoquinone in the dark, J. Biol. Chem. 278 (2003) 13554-13560.
28. N. Bondarava, C. M. Gross, M. Mubarakshina, J. R. Golecki, G. N. Johnson, A. Krieger-Liszkay, Putative function of cytochrome $b_{559}$ as a plastoquinol oxidase, Physiol. Plant. 138 (2010) 463-473.
29. C. A. Buser. B. A. Diner. G. W. Brudvig, photooxidation of cytochrome $b_{559}$ in oxygen-evolving photosystem II, Biochemistry 31 (1992) 11449-11459.
30. J. Barber, J. De Las Rivas, A functional model for the role of cytochrome $b_{559}$ in the protection against donor and acceptor side photoinhibition, Proc. Natl. Acad. Sci. U.S.A. 90 (1993) 10942-10946.
31. C.-H. Hung, J.-Y. Huang, Y.-F. Chiu, H.-A. Chu, Site-directed mutagenesis on the heme axial-ligands of cytochrome b559 in photosystem II by using cyanobacteria *Synechocystis* PCC 6803, Biochim. Biophys. Acta 1767 (2007) 686-693.
32. C. H. Hung, H. J. Hwang, Y.-F. Chiu, Y. H. Chen, S. C. Ke, R. L. Burnap, H.-A. Chu, Spectroscopic and functional characterizations of *Synechocystsis* 6803 mutant on and near the heme axial-ligand of cytochrome B559 in photosystem II. J. Biol. Chem. 285 (2010) 5653-5663.
33. Y. F. Chiu, Y. H. Chen, M. Roncel, P. L. Dilbeck, J. Y. Huang, S. C. Ke, J. M. Ortega, R. L. Burnap, H.-A. Chu, Spectroscopic and functional characterization of cyanobacterium *Synechocystis* PCC 6803 mutants on the cytoplasmic-side of cytochrome b559 in photosystem II. Biochim. Biophys. Acta 1827 (2013) 507-519.
34. Y. F. Chiu, W. C. Lin, C. M. Wu, Y. H. Chen, C. H. Hung, S. C. Ke, H.-A. Chu, Identification and characterization of a cytochrome $b_{559}$ *Synechocystsis* 6803 mutant spontaneously generated from DCMU-inhibited photoheterotrophical growth conditions. Biochim. Biophys. Acta, Bioenerg. 1787 (2009) 1179-1188.
35. R. de Wijn, H. J. van Gorkom, Kinetics of electron transfer from Q(A) to Q(B) in photosystem II, Biochemistry 40 (2001) 11912-119222.
36. D. Bruce, S. Brimble, D. A. Bryant, State transitions in a phycobilisome-less mutant of the cyanobacterium *Synechococcus* sp. PCC 7002, Biochim. Biophys. Acta, Bioenerg. 974 (1989) 66-73.
37. K. Kondo, C. W. Mullineaux, M. Ikeuchi, Distinct roles of CpcG1-phycobilisome and CpcG2-phycobilisome in state transitions in a cyanobacterium *Synechocystis* sp. PCC 6803, Photosynth. Res. 99 (2009) 217-225.
38. J. Barber, E. P. Morris, P.C.A. da Fonseca, Interaction of allophycocyanin core complex with photosystem II, Photochem. Photobiol. Sci. 2 (2003) 536-541.
39. H. Zhang, H. Liu, D. M. Niedzwiedzki, M. Prado, J. Jiang, M. L. Gross, and R. E. Blankenship, Molecular mechanism of photoactivation and structural location of the cyanobacterial orange carotenoid protein, Biochemistry 53 (2014) 13-19.
40. I. M. Machado, S. Atsumi, Cyanobacterial biofuel production, J. Biotechnol. 162 (2012) 50-56.
41. P. G. Stephenson, C. M. Moore, M. J. Terry, M. V. Zubkov, T. S. Bibby, Improving photosynthesis for algal biofuels: toward a green revolution, Trend. Biotech. 29 (2011) 615-623.
42. Pistorius A M A, DeGrip W J, Egorova-Zache T A (2009) Monitoring of biomass composition from microbiological sources by means of FT-IR spectroscopy, Biotechno. Bioeng. 103: 123-129

What is claimed is:

1. A mutant *Synechocystis* cell, expressing a mutant *Synechocystis* cytochrome polypeptide selected from the group consisting of:
   (a) a mutant *Synechocystis* cytochrome b559 α polypeptide, which has alanine (A) at the position corresponding to position S23 in SEQ ID NO: 1;
   (b) a mutant *Synechocystis* cytochrome b559 β polypeptide, which has (i) alanine (A) or valine (V) at the position corresponding to position S28 in SEQ ID NO: 2, or (ii) phenylalanine (F) at the position corresponding to position V32 in SEQ ID NO: 2; and
   (c) a mutant *Synechocystis* cytochrome PsbJ polypeptide, which has (i) phenylalanine (F) or arginine (R) at the position corresponding to position A16 in SEQ ID NO: 3, or (ii) phenylalanine (F) at the position corresponding to position A20 in SEQ ID NO: 3.

2. The mutant *Synechocystis* cell of claim 1, which exhibits weakened effects of blue-light-induced nonphotochemical fluorescence quenching (NPQ) when compared with its wild-type counterpart under the same conditions.

3. The mutant *Synechocystis* cell of claim 1, which exhibits enhanced effects of state transitions under medium blue light, when compared with its wild-type counterpart under the same conditions.

4. The mutant *Synechocystis* cell of claim 1, which exhibits increased photosynthetic growth rate and/or biomass production, when compared with its wild-type counterpart under the same conditions.

5. The mutant *Synechocystis* cell of claim 1, which expresses a substantially level of an orange carotenoid protein (OCP) relative to its wild-type counterpart under the same conditions.

6. The mutant *Synechocystis* cell of claim 1, which comprises a psbE gene encoding a mutant *Synechocystis* b559 α polypeptide of SEQ ID NO: 4.

7. The mutant *Synechocystis* cell of claim 1, which comprises a psbF gene encoding a mutant *Synechocystis* b559 β polypeptide of SEQ ID NO: 5, 6 or 7.

8. The mutant *Synechocystis* cell of claim 1, which comprises a psbJ gene encoding a mutant *Synechocystis* cytochrome PsbJ polypeptide of SEQ ID NO: 8, 9 or 10.

9. The mutant *Synechocystis* cell of claim 1, wherein the mutant *Synechocystis* cytochrome polypeptide is selected from the group consisting of: S23Aα, S28Aβ, S28Vβ, V32Fβ, A16FJ, A16RJ and A20FJ.

10. A recombinant nucleic acid comprising a nucleotide sequence encoding a mutant *Synechocystis* cytochrome polypeptide selected from the group consisting of:
    (a) a mutant *Synechocystis* cytochrome b559 α polypeptide, which has alanine (A) at the position corresponding to position S23 in SEQ ID NO: 1;
    (b) a mutant *Synechocystis* cytochrome b559 β polypeptide, which has (i) alanine (A) or valine (V) at the position corresponding to position S28 in SEQ ID NO: 2, or (ii) phenylalanine (F) at the position corresponding to position V32 in SEQ ID NO: 2; and
    (c) a mutant *Synechocystis* cytochrome PsbJ polypeptide, which has (i) phenylalanine (F) or arginine (R) at the position corresponding to position A16 in SEQ ID NO: 3, or (ii) phenylalanine (F) at the position corresponding to position A20 in SEQ ID NO: 3.

11. The recombinant nucleic acid of claim 10, wherein the mutant *Synechocystis* cytochrome polypeptide is selected from the group consisting of S23Aα, S28Aβ, S28Vβ, V32Fβ, A16FJ, A16RJ and A20FJ.

12. The recombinant nucleic acid of claim 10, wherein the mutant *Synechocystis* cytochrome polypeptide is a mutant *Synechocystis* cytochrome b559 α polypeptide of SEQ ID NO: 4, a mutant *Synechocystis* cytochrome b559 62 polypeptide of SEQ ID NO: 5, 6 or 7, or a mutant *Synechocystis* cytochrome PsbJ polypeptide of SEQ ID NO: 8, 9 or 10.

13. A host cell comprising the recombinant nucleic acid of claim 10.

14. A method for producing biomass or a biomolecule comprising culturing a mutant *Synechocystis* cell of claim 1 under light conditions in a suitable medium and harvesting biomass or a biomolecule from the culture.

15. The method of claim 14, wherein the biomolecule is selected from the group consisting of carbohydrates, fatty acids, proteins, oils, amino acids, peptide, pigments, terpenoid, carotenoid, vitamin, or other high-value biomolecules.

* * * * *

UNITED STATES PATENT AND TRADEMARK OFFICE
CERTIFICATE OF CORRECTION

PATENT NO. : 9,803,179 B2  
APPLICATION NO. : 14/820866  
DATED : October 31, 2017  
INVENTOR(S) : Hsiu-An Chu et al.

Page 1 of 1

It is certified that error appears in the above-identified patent and that said Letters Patent is hereby corrected as shown below:

In the Claims

At Column 28, Claim 12, Line 42, "cytochrome b559 62 polypeptide" should read -- cytochrome b559 β polypeptide --

Signed and Sealed this  
Sixth Day of February, 2018

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 19

<210> SEQ ID NO 1
<211> LENGTH: 80
<212> TYPE: PRT
<213> ORGANISM: Synechocystis PCC6803

<400> SEQUENCE: 1

Ser Gly Thr Thr Gly Glu Arg Pro Phe Ser Asp Ile Val Thr Ser Ile
1               5                   10                  15

Arg Tyr Trp Val Ile His Ser Ile Thr Ile Pro Met Leu Phe Ile Ala
            20                  25                  30

Gly Trp Leu Phe Val Ser Thr Gly Leu Ala Tyr Asp Ala Phe Gly Thr
        35                  40                  45

Pro Arg Pro Asp Glu Tyr Phe Thr Gln Thr Arg Gln Glu Leu Pro Ile
    50                  55                  60

Leu Gln Glu Arg Tyr Asp Ile Asn Gln Glu Ile Gln Glu Phe Asn Gln
65                  70                  75                  80

<210> SEQ ID NO 2
<211> LENGTH: 43
<212> TYPE: PRT
<213> ORGANISM: Synechocystis PCC6803

<400> SEQUENCE: 2
```

```
Ala Thr Gln Asn Pro Asn Gln Pro Val Thr Tyr Pro Ile Phe Thr Val
1               5                   10                  15

Arg Trp Leu Ala Val His Thr Leu Ala Val Pro Ser Val Phe Phe Val
                20                  25                  30

Gly Ala Ile Ala Ala Met Gln Phe Ile Gln Arg
            35                  40
```

<210> SEQ ID NO 3
<211> LENGTH: 39
<212> TYPE: PRT
<213> ORGANISM: Synechocystis PCC6803

<400> SEQUENCE: 3

```
Met Phe Ala Glu Gly Arg Ile Pro Leu Trp Val Val Gly Val Val Ala
1               5                   10                  15

Gly Ile Gly Ala Ile Gly Val Leu Gly Leu Phe Phe Tyr Gly Ala Tyr
                20                  25                  30

Ala Gly Leu Gly Ser Ser Met
            35
```

<210> SEQ ID NO 4
<211> LENGTH: 80
<212> TYPE: PRT
<213> ORGANISM: Synechocystis PCC6803

<400> SEQUENCE: 4

```
Ser Gly Thr Thr Gly Glu Arg Pro Phe Ser Asp Ile Val Thr Ser Ile
1               5                   10                  15

Arg Tyr Trp Val Ile His Ala Ile Thr Ile Pro Met Leu Phe Ile Ala
                20                  25                  30

Gly Trp Leu Phe Val Ser Thr Gly Leu Ala Tyr Asp Ala Phe Gly Thr
            35                  40                  45

Pro Arg Pro Asp Glu Tyr Phe Thr Gln Thr Arg Gln Glu Leu Pro Ile
        50                  55                  60

Leu Gln Glu Arg Tyr Asp Ile Asn Gln Glu Ile Gln Glu Phe Asn Gln
65                  70                  75                  80
```

<210> SEQ ID NO 5
<211> LENGTH: 43
<212> TYPE: PRT
<213> ORGANISM: Synechocystis PCC6803

<400> SEQUENCE: 5

```
Ala Thr Gln Asn Pro Asn Gln Pro Val Thr Tyr Pro Ile Phe Thr Val
1               5                   10                  15

Arg Trp Leu Ala Val His Thr Leu Ala Val Pro Ala Val Phe Phe Val
                20                  25                  30

Gly Ala Ile Ala Ala Met Gln Phe Ile Gln Arg
            35                  40
```

<210> SEQ ID NO 6
<211> LENGTH: 43
<212> TYPE: PRT
<213> ORGANISM: Synechocystis PCC6803

<400> SEQUENCE: 6

```
Ala Thr Gln Asn Pro Asn Gln Pro Val Thr Tyr Pro Ile Phe Thr Val
1               5                   10                  15

Arg Trp Leu Ala Val His Thr Leu Ala Val Pro Val Val Phe Phe Val
```

-continued

```
                  20                  25                  30

Gly Ala Ile Ala Ala Met Gln Phe Ile Gln Arg
        35                  40

<210> SEQ ID NO 7
<211> LENGTH: 43
<212> TYPE: PRT
<213> ORGANISM: Synechocystis PCC6803

<400> SEQUENCE: 7

Ala Thr Gln Asn Pro Asn Gln Pro Val Thr Tyr Pro Ile Phe Thr Val
1               5                   10                  15

Arg Trp Leu Ala Val His Thr Leu Ala Val Pro Ser Val Phe Phe Phe
            20                  25                  30

Gly Ala Ile Ala Ala Met Gln Phe Ile Gln Arg
        35                  40

<210> SEQ ID NO 8
<211> LENGTH: 39
<212> TYPE: PRT
<213> ORGANISM: Synechocystis PCC6803

<400> SEQUENCE: 8

Met Phe Ala Glu Gly Arg Ile Pro Leu Trp Val Val Gly Val Val Phe
1               5                   10                  15

Gly Ile Gly Ala Ile Gly Val Leu Gly Leu Phe Phe Tyr Gly Ala Tyr
            20                  25                  30

Ala Gly Leu Gly Ser Ser Met
        35

<210> SEQ ID NO 9
<211> LENGTH: 39
<212> TYPE: PRT
<213> ORGANISM: Synechocystis PCC6803

<400> SEQUENCE: 9

Met Phe Ala Glu Gly Arg Ile Pro Leu Trp Val Val Gly Val Val Arg
1               5                   10                  15

Gly Ile Gly Ala Ile Gly Val Leu Gly Leu Phe Phe Tyr Gly Ala Tyr
            20                  25                  30

Ala Gly Leu Gly Ser Ser Met
        35

<210> SEQ ID NO 10
<211> LENGTH: 39
<212> TYPE: PRT
<213> ORGANISM: Synechocystis PCC6803

<400> SEQUENCE: 10

Met Phe Ala Glu Gly Arg Ile Pro Leu Trp Val Val Gly Val Val Ala
1               5                   10                  15

Gly Ile Gly Phe Ile Gly Val Leu Gly Leu Phe Phe Tyr Gly Ala Tyr
            20                  25                  30

Ala Gly Leu Gly Ser Ser Met
        35

<210> SEQ ID NO 11
<211> LENGTH: 81
<212> TYPE: PRT
<213> ORGANISM: Cyanothece PCC7822
```

```
<400> SEQUENCE: 11

Met Ser Gly Thr Thr Gly Glu Arg Pro Phe Ser Asp Ile Val Thr Ser
1               5                   10                  15

Ile Arg Tyr Trp Val Ile His Ser Ile Thr Ile Pro Met Leu Phe Ile
            20                  25                  30

Ala Gly Trp Leu Phe Val Ser Thr Gly Leu Ala Tyr Asp Val Phe Gly
        35                  40                  45

Thr Pro Arg Pro Asp Gln Tyr Phe Thr Gln Arg Leu Glu Leu Pro
    50                  55                  60

Ile Leu Lys Glu Arg Tyr Asn Thr Asp Gln Gln Ile Lys Glu Phe Asn
65                  70                  75                  80

Lys

<210> SEQ ID NO 12
<211> LENGTH: 82
<212> TYPE: PRT
<213> ORGANISM: Anabaena

<400> SEQUENCE: 12

Met Ser Gly Thr Thr Gly Glu Arg Pro Phe Ser Asp Ile Val Thr Ser
1               5                   10                  15

Ile Arg Tyr Trp Val Ile His Ser Ile Thr Ile Pro Ala Leu Phe Ile
            20                  25                  30

Ala Gly Trp Leu Phe Val Ser Thr Gly Leu Ala Tyr Asp Val Phe Gly
        35                  40                  45

Thr Pro Arg Pro Asp Glu Tyr Tyr Thr Gln Ala Arg Gln Glu Leu Pro
    50                  55                  60

Ile Val Asn Asn Arg Phe Glu Ala Lys Lys Gln Val Glu Gln Leu Ile
65                  70                  75                  80

Gln Lys

<210> SEQ ID NO 13
<211> LENGTH: 82
<212> TYPE: PRT
<213> ORGANISM: Arthrospira platensis

<400> SEQUENCE: 13

Met Ala Gly Thr Thr Gly Glu Arg Pro Phe Gly Asp Ile Ile Thr Ser
1               5                   10                  15

Val Arg Tyr Trp Val Ile His Ser Leu Thr Ile Pro Ala Leu Phe Ile
            20                  25                  30

Ala Gly Trp Leu Phe Val Ser Thr Gly Leu Ala Tyr Asp Ala Phe Gly
        35                  40                  45

Thr Pro Arg Pro Asn Glu Tyr Phe Thr Gln Arg Gln Glu Leu Pro
    50                  55                  60

Ile Ile Thr Glu Arg Gln Asp Ser Lys Thr Gln Ile Gln Gln Phe Ile
65                  70                  75                  80

Ala Lys

<210> SEQ ID NO 14
<211> LENGTH: 44
<212> TYPE: PRT
<213> ORGANISM: Cyanothece PCC7822

<400> SEQUENCE: 14

Met Ala Asn Thr Thr Gly Asn Gln Pro Val Ser Tyr Pro Ile Phe Thr
1               5                   10                  15
```

```
Val Arg Trp Leu Ala Val His Thr Leu Ala Val Pro Thr Val Phe Phe
         20                  25                  30

Ile Gly Ala Ile Ala Ala Met Gln Phe Ile Gln Arg
         35                  40
```

<210> SEQ ID NO 15
<211> LENGTH: 45
<212> TYPE: PRT
<213> ORGANISM: Anabaena ATCC29413

<400> SEQUENCE: 15

```
Met Thr Ser Gly Asn Asn Ile Asn Gln Pro Val Thr Tyr Pro Ile Phe
1               5                   10                  15

Thr Val Arg Trp Leu Ala Val His Thr Leu Ala Val Pro Thr Val Phe
             20                  25                  30

Phe Leu Gly Ala Ile Ala Ser Met Gln Phe Ile Gln Arg
             35                  40                  45
```

<210> SEQ ID NO 16
<211> LENGTH: 44
<212> TYPE: PRT
<213> ORGANISM: Arthrospira platensis

<400> SEQUENCE: 16

```
Met Thr Asn Ala Asn Gln Asn Gln Pro Ile Thr Tyr Pro Ile Phe Thr
1               5                   10                  15

Val Arg Trp Leu Ala Val His Thr Leu Ala Val Pro Thr Val Phe Phe
             20                  25                  30

Leu Gly Ala Ile Ala Ala Met Gln Phe Ile Gln Arg
             35                  40
```

<210> SEQ ID NO 17
<211> LENGTH: 39
<212> TYPE: PRT
<213> ORGANISM: Cyanothece PCC7822

<400> SEQUENCE: 17

```
Met Phe Ala Glu Gly Arg Ile Pro Leu Trp Val Val Ala Val Val Ala
1               5                   10                  15

Gly Leu Gly Val Ile Ala Val Val Gly Leu Phe Phe Tyr Gly Ala Tyr
             20                  25                  30

Ala Gly Leu Gly Ser Ser Leu
             35
```

<210> SEQ ID NO 18
<211> LENGTH: 48
<212> TYPE: PRT
<213> ORGANISM: Anabaena ATCC29413

<400> SEQUENCE: 18

```
Met Leu Leu Arg Glu Glu Lys Ala Val Ser Ala Gly Ser Gly Arg Ile
1               5                   10                  15

Pro Leu Trp Val Val Ala Thr Ile Ala Gly Leu Gly Val Ile Thr Val
             20                  25                  30

Val Gly Ile Phe Phe Tyr Gly Ala Tyr Ala Gly Leu Gly Ser Ser Ile
             35                  40                  45
```

<210> SEQ ID NO 19
<211> LENGTH: 39
<212> TYPE: PRT

```
<213> ORGANISM: Arthrospira platensis

<400> SEQUENCE: 19

Met Ser Gly Asp Ala Lys Leu Pro Leu Trp Leu Ile Ala Thr Val Ala
1               5                   10                  15

Gly Thr Gly Val Leu Val Val Val Gly Leu Phe Phe Tyr Gly Ala Tyr
            20                  25                  30

Val Gly Val Gly Ser Ala Leu
        35
```